(12) United States Patent
Maeda et al.

(10) Patent No.: US 8,759,540 B2
(45) Date of Patent: *Jun. 24, 2014

(54) COLOR TONE CORRECTING AGENT, SQUARYLIUM COMPOUND AND OPTICAL FILTER

(75) Inventors: Yosuke Maeda, Tokyo (JP); Tatsuya Ishida, Tokyo (JP)

(73) Assignee: Adeka Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/501,168

(22) PCT Filed: Dec. 3, 2010

(86) PCT No.: PCT/JP2010/071698
§ 371 (c)(1),
(2), (4) Date: Apr. 10, 2012

(87) PCT Pub. No.: WO2011/086785
PCT Pub. Date: Jul. 21, 2011

(65) Prior Publication Data
US 2012/0197026 A1    Aug. 2, 2012

(30) Foreign Application Priority Data

Jan. 15, 2010  (JP) ................... 2010-006804

(51) Int. Cl.
C09B 31/15 (2006.01)
G02B 5/22 (2006.01)

(52) U.S. Cl.
USPC ........................................ 548/455

(58) Field of Classification Search
USPC ........................................ 548/455
See application file for complete search history.

(56) References Cited

U.S. PATENT DOCUMENTS

| | | | | |
|---|---|---|---|---|
| 5,403,686 | A * | 4/1995 | Bugner et al. | 430/59.1 |
| 5,763,134 | A * | 6/1998 | Busman et al. | 430/157 |
| 6,605,416 | B2 | 8/2003 | Busman et al. | |
| RE38,251 | E | 9/2003 | Busman et al. | |
| 7,745,632 | B2 * | 6/2010 | Aoyama et al. | 548/121 |
| 2001/0008748 | A1 | 7/2001 | Busman et al. | |
| 2001/0055080 | A1* | 12/2001 | Naito et al. | 349/79 |
| 2007/0148556 | A1* | 6/2007 | Maeno et al. | 430/1 |
| 2008/0207918 | A1 | 8/2008 | Aoyama et al. | |
| 2010/0003445 | A1* | 1/2010 | Yano et al. | 428/64.4 |
| 2010/0204474 | A1 | 8/2010 | Aoyama et al. | |

FOREIGN PATENT DOCUMENTS

| | | |
|---|---|---|
| EP | 0645680 | 3/1995 |
| GB | 2426072 | 11/2006 |
| JP | 4-45160 | 2/1992 |
| JP | 6-263732 | 9/1994 |
| JP | 6-287210 | 10/1994 |
| JP | 7-160028 | 6/1995 |
| JP | 7-287393 | 10/1995 |
| JP | 2000-043175 | 2/2000 |
| JP | 2001-513903 | 9/2001 |
| JP | 2005-181872 | 7/2005 |
| JP | 2005-331545 | 12/2005 |
| JP | 2006-312710 | 11/2006 |
| JP | 2007-131818 | 5/2007 |
| JP | 2009-040860 | 2/2009 |
| WO | WO 97/43695 | 11/1997 |
| WO | WO 2005118839 A1 * | 12/2005 |
| WO | WO 2006109618 A1 * | 10/2006 |
| WO | WO 2008/023657 | 2/2008 |
| WO | WO 2008/069268 | 6/2008 |

OTHER PUBLICATIONS

International Search Report, PCT/JP2010/071698, Jan. 25, 2011.
Chinese Office Action dated Apr. 1, 2013 in corresponding Chinese Patent Application No. 201080044656.3.
Supplementary European Search Report dated May 23, 2013 in corresponding European Patent Application No. 10843140.4.
Nobuhiro Kuramoto, "The role of excited singlet molecular oxygen in the photodegradation of functional squarylium dyes", Journal of the Society of Dyers and Colourists, Bradford, GB, vol. 106, No. 5-6, May 1, 1990, pp. 181-186, XP009169440.
Zhongyu Li et al., "Large third-order optical nonlinearities of centrosymmetric squaraines with heterocyclic donor groups measured by femtosecond degenerate four-wave mixing technique", Chemical Physics Letters, Elsevier BV, NL, vol. 441, No. 1-3, May 31, 2007, pp. 123-126, XP022100018.
A.P. Piechowski et al., "Desirable Properties of Photovoltaic Dyes", Journal of Physical Chemistry, American Chemical Society, US, vol. 88, No. 5, Jan. 1, 1984, pp. 934-950, XP002464705.
Sergio Tatay et al., "Kinetic competition in liquid electrolyte and solid-state cyanine dye sensitized solar cells", Journal of Materials Chemistry, vol. 17, No. 29, Jan. 1, 2007, pp. 3037-3044, XP055061848.

* cited by examiner

Primary Examiner — Nyeemah A Grazier
(74) Attorney, Agent, or Firm — Young & Thompson

(57) ABSTRACT

The present invention provides a color tone correcting agent having suitable heat resistance for use in an optical filter, a novel squarylium compound that is specifically preferable as the color tone correcting agent, and an optical filter including the color tone correcting agent. Specifically, the present invention provides a color tone correcting agent including a squarylium compound represented by the general formula (1), a novel squarylium compound which is represented by the general formula (4) and is preferable as the color tone correcting agent, and an optical filter including the color tone correcting agent. The general formula (1) and (4) are each as defined in the specification.

9 Claims, No Drawings

COLOR TONE CORRECTING AGENT, SQUARYLIUM COMPOUND AND OPTICAL FILTER

TECHNICAL FIELD

The present invention relates to a color tone correcting agent including a squarylium compound having a specific structure, a novel squarylium compound that is specifically preferable as the color tone correcting agent, and an optical filter including the color tone correcting agent. The optical filter is specifically useful as an optical filter for an image display apparatus and an illumination apparatus.

BACKGROUND ART

Compounds having absorption of a large intensity against specific light are used as color tone correcting agents for recording layers of optical recording media such as CD-Rs, DVD-Rs, DVD+Rs and blue laser recording discs, image display apparatuses such as liquid crystal display apparatuses (LCDs), plasma display panels (PDPs), electroluminescence displays (ELDs), cathode ray tube display apparatuses (CRT), fluorescence display tubes and field emission displays, CCD image sensors, CMOS image sensors; LED illuminations, and the like.

For a color tone correcting agent, light absorption property for selectively absorbing light at a required wavelength area, solubility or compatibility in organic solvents and synthetic resins that are necessary for processing into a filter or film, and stability against light and heat for maintaining performances are required.

As such color tone correcting agent, uses of a cyanine compound and a squarylium compound each having an indole backbone have been reported. For example, Patent Literature 1 discloses a squarylium compound having an indole backbone having a ferrocene group, which has fine solubility and light resistance. Furthermore, Patent Literature 2 discloses a trimethinecyanine compound having $CF_3$ at the 5-position or $NO_2$ at the 4- or 6-position, which shows precipitous absorption and has fine wet heat resistance and light resistance. Furthermore, Patent Literature 3 discloses a trimethinecyanine compound having $CF_3$ and $NO_2$ at the 5-position. However, in order to use the compounds as a color tone correcting agent for an optical filter, further improvement of heat resistance is demanded so as to withstand the processing temperature of the optical filter.

CITATION LIST

Patent Literatures

Patent Literature 1: Japanese Patent Application Laid-Open (JP-A) No. 2006-312710 (U.S. Patent Application Publication No. 2008/0207918A1)
Patent Literature 2: JP-A No. 2005-331545
Patent Literature 3: JP-A No. 2007-131818

DISCLOSURE OF THE INVENTION

Problem to be Solved by the Invention

Therefore, the object of the present invention is to provide a color tone correcting agent having suitable heat resistance for use in an optical filter, a novel squarylium compound that is specifically preferable as the color tone correcting agent, and an optical filter including the color tone correcting agent.

Means for Solving the Problem

The present inventors have made a great deal of consideration and consequently found that a squarylium compound having a specific structure has high heat resistance and the above-mentioned object may be achieved by using this as a color tone correcting agent.

The present invention has been made based on the above-mentioned finding, and provides a color tone correcting agent including a squarylium compound represented by the following general formula (1):

[Chemical Formula 1]

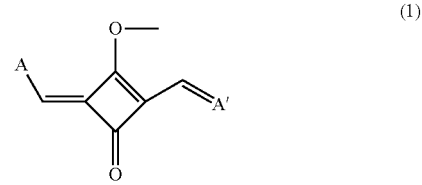

(1)

wherein

A is a group selected from (a) to (k) in the following Group I, and

A' is a group selected from (a') to (k') in the following Group II:

[Chemical Formula 2]

Group I

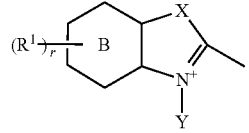

(a)

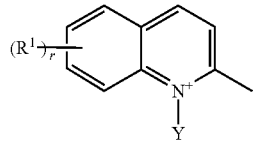

(b)

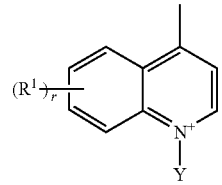

(c)

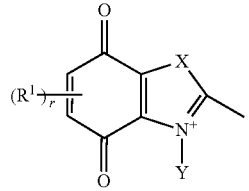

(d)

-continued
(e)
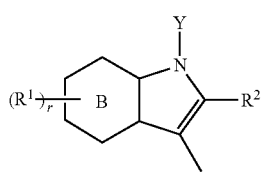
(f)
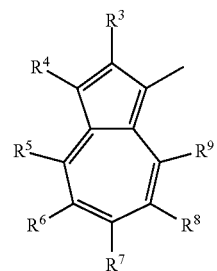
(g)
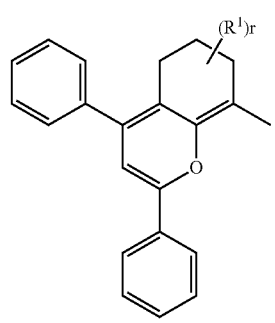
(h)
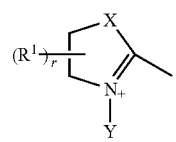
(i)
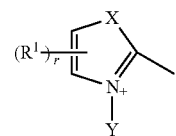
(j)
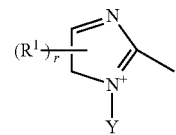
(k)
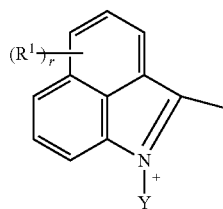
[Chemical Formula 3]
Group II
(a')
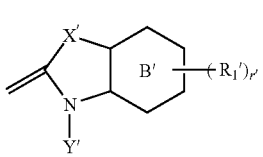
-continued
(b')
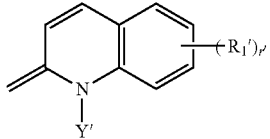
(c')
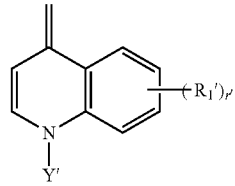
(d')
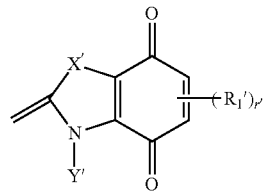
(e')
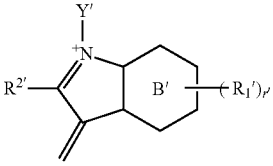
(f')
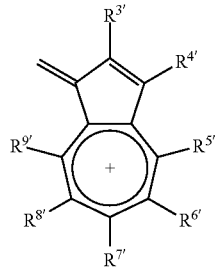
(g')
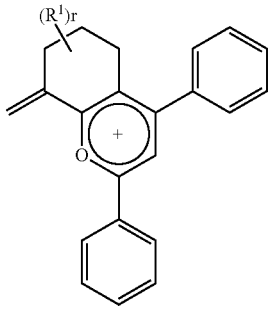
(h')
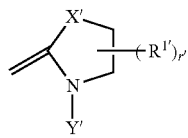
(i')
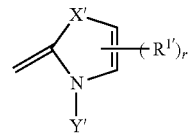

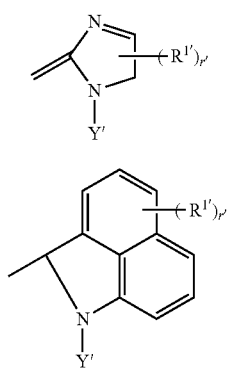

(j')

(k')

wherein ring B and ring B' each represents a benzene ring, a naphthalene ring, a phenanthrene ring or a pyridine ring, $R^1$ and $R^{1'}$ each represents a halogen atom, a nitro group, a cyano group, an aryl group having 6 to 30 carbon atoms, an arylalkyl group having 7 to 30 carbon atoms, an alkyl group having 1 to 8 carbon atom(s), a halogen-substituted alkyl group having 1 to 8 carbon atom(s), an alkoxy group having 1 to 8 carbon atom(s), a halogen-substituted alkoxy group having 1 to 8 carbon atom(s) or an ether group having 2 to 8 carbon atoms, $R^2$ and $R^{2'}$ each represents a hydrogen atom, a halogen atom, an aryl group having 6 to 30 carbon atoms, an arylalkyl group having 7 to 30 carbon atoms or an alkyl group having 1 to 8 carbon atom(s);

$R^3$ to $R^9$ and $R^{3'}$ to $R^{9'}$ each represents a hydrogen atom, a halogen atom, an alkyl group having 1 to 8 carbon atom(s) or a group that forms a condensed ring with the adjacent substituent, X and X' each represents an oxygen atom, a sulfur atom, a serenium atom, —$CR^{51}R^{52}$—, a cycloalkane-1,1-diyl group having 3 to 6 carbon atoms, —NH— or —$NY^2$—, wherein $R^{51}$ and $R^{52}$ each represents a hydrogen atom, a group represented by the following general formula (11) or (12), an alkyl group having 1 to 20 carbon atom(s) optionally substituted by a hydroxyl group, a halogen atom, a cyano group or a nitro group, an aryl group having 6 to 30 carbon atoms optionally substituted by a hydroxyl group, a halogen atom, a cyano group or a nitro group, or an arylalkyl group having 7 to 30 carbon atoms optionally substituted by a hydroxyl group, a halogen atom, a cyano group or a nitro group, Y, Y' and $Y^2$ each represents a hydrogen atom, an alkyl group having 1 to 20 carbon atom(s) optionally substituted by a hydroxyl group, a halogen atom, a cyano group or a nitro group, an aryl group having 6 to 30 carbon atoms optionally substituted by a hydroxyl group, a halogen atom, a cyano group or a nitro group, or an arylalkyl group having 7 to 30 carbon atoms optionally substituted by a hydroxyl group, a halogen atom, a cyano group or a nitro group, wherein the methylene group(s) in the alkyl groups and arylalkyl groups in the Y, Y' and $Y^2$ may be interrupted by —O—, —S—, —CO—, —COO—, —OCO—, —$SO_2$—, —NH—, —CONH—, —NHCO—, —N=CH— or —CH=CH—, and r and r' each represents 0, or a number of possible substitution in (a) to (k) or (a') to (k'),

[Chemical Formula 4]

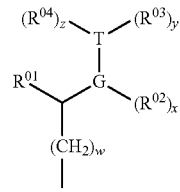

(11)

(12)

wherein in the above-mentioned general formula (11), the bond between G and T is a double bond, a conjugate double bond or a triple bond, G represents a carbon atom, T represents a carbon atom, an oxygen atom or a nitrogen atom, provided that when T is an oxygen atom, y and z are 0, and when T is a nitrogen atom, y+z is 0 or 1, w represents a number of 0 to 4, x, y and z each represents 0 or 1, $R^{O1}$, $R^{O2}$, $R^{O3}$ and $R^{O4}$ each represents a hydrogen atom, a hydroxyl group, a nitro group, a cyano group, a halogen atom or an alkyl group having 1 to 4 carbon atom(s) optionally having substituent(s), wherein the methylene group(s) in the alkyl group may be interrupted by —O— or —CO—, and $R^{O1}$ and $R^{O4}$ may bind to form a cycloalkene ring or a hetero ring, and in the above-mentioned general formula (12), the bond between G' and T' is a double bond or a conjugate double bond, G' represents a carbon atom, T' represents a carbon atom or a nitrogen atom, and w' represents a number of 0 to 4, $R^{O1'}$ represents a hydrogen atom, a hydroxyl group, a nitro group, a cyano group, a halogen atom or an alkyl group having 1 to 4 carbon atom(s) optionally having substituent(s), wherein the methylene group(s) in the alkyl group may be interrupted by —O— or —CO—, the ring comprising G' and T' represents a 5-membered ring optionally comprising hetero atom(s), a 6-membered ring optionally comprising hetero atom(s), a quinoline ring, an isoquinoline ring or an anthraquinone ring, wherein the ring comprising these G' and T' may be substituted by a halogen atom, a hydroxyl group, a nitro group, a cyano group, an alkyl group having 1 to 4 carbon atom(s) or an alkoxy group having 1 to 4 carbon atom(s).

Furthermore, the present invention provides a novel squarylium compound represented by the following general formula (4):

[Chemical Formula 5]

(4)

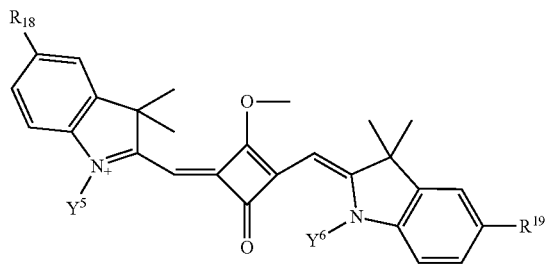

wherein $R^{18}$ and $R^{19}$ each represents a nitro group, a trifluoromethane group or a methoxy group, and $Y^5$ and $Y^6$ each represents an alkyl group having 1 to 18 carbon atom(s), an ether group having 3 to 18 carbon atoms, an aryl group having 6 to 18 carbon atoms or an arylalkyl group having 7 to 18 carbon atoms.

Furthermore, the present invention provides an optical filter including at lease one kind of the above-mentioned color tone correcting agents.

Effect of the Invention

According to the present invention, a color tone correcting agent having fine heat resistance and an optical filter including this can be provided.

BEST MODES FOR CARRYING OUT THE INVENTION

Hereinafter the present invention will be explained in detail based on the preferable exemplary embodiments.

First, the color tone correcting agent of the present invention will be explained.

The color tone correcting agent of the present invention includes the squarylium compound represented by the above-mentioned general formula (1), preferably a squarylium compound represented by the general formula (2), (3) or (4) mentioned below. In the present invention, a color tone correcting agent refers to an agent having a function to absorb specific visible light to improve qualities of light sources, images, movies, light signals, visual information and the like.

In the above-mentioned general formula (1), examples of the halogen atom represented by $R^1$ and $R^{1'}$ may include fluorine, chlorine, bromine and iodine;

examples of the aryl group having 6 to 30 carbon atoms may include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl)phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-ditert-butylphenyl, 2,5-ditert-butylphenyl, 2,6-ditert-butylphenyl, 2,4-ditert-pentylphenyl, 2,5-ditert-amylphenyl, 2,5-ditert-octylphenyl, 2,4-dicumylphenyl, cyclohexylphenyl, biphenyl, 2,4,5-trimethylphenyl and the like;

examples of the arylalkyl group having 7 to 30 carbon atoms may include benzyl, phenetyl, 2-phenylpropan-2-yl, diphenylmethyl, triphenylmethyl, styryl, cinnamyl and the like;

examples of the alkyl group having 1 to 8 carbon atom(s) may include methyl, ethyl, propyl, isopropyl, butyl, sec-butyl, tert-butyl, isobutyl, amyl, isoamyl, tert-amyl, hexyl, 2-hexyl, 3-hexyl, cyclohexyl, 1-methylcyclohexyl, heptyl, 2-heptyl, 3-heptyl, isoheptyl, tert-heptyl, 1-octyl, isooctyl, tert-octyl and the like;

examples of the halogen-substituted alkyl group having 1 to 8 carbon atom(s) may include alkyl groups in which at least one hydrogen atom has been substituted by a halogen atom such as chloromethyl, dichloromethyl, trichloromethyl, fluoromethyl, fluoromethyl, trifluoromethyl and nonafluorobutyl, and the like;

examples of the alkoxy group having 1 to 8 carbon atom(s) may include methyloxy, ethyloxy, isopropyloxy, propyloxy, butyloxy, pentyloxy, isopentyloxy, hexyloxy, heptyloxy, octyloxy, 2-ethylhexyloxy and the like;

examples of the halogen-substituted alkoxy group having 1 to 8 carbon atom(s) may include these alkoxy groups in which at least one hydrogen atom has been substituted by a halogen atom such as chloromethyloxy, dichloromethyloxy, trichloromethyloxy, fluoromethyloxy, fluoromethyloxy, trifluoromethyloxy and nonafluorobutyloxy, and the like; and examples of the ether group having 2 to 8 carbon atoms may include 2-methoxyethyl, 2-(2-methoxy)ethoxyethyl, 2-ethoxyethyl, 2-butoxyethyl, 4-methoxybutyl, 3-methoxybutyl and the like.

Examples of the halogen atom, aryl group having 6 to 30 carbon atoms, arylalkyl group having 7 to 30 carbon atoms and alkyl group having 1 to 8 carbon atom(s) represented by $R^2$ and $R^{2'}$ may include the groups that are exemplified in the explanation for the above-mentioned $R^1$, and the like.

Examples of the halogen atom and alkyl group having 1 to 8 carbon atom(s) represented by $R^3$ to $R^9$ and $R^{3'}$ to $R^{9'}$ may include the groups that are exemplified in the explanation for the above-mentioned $R^1$, and the like, and examples of the condensed ring constituted by the group that forms a condensed ring with the adjacent substituent may include aromatic rings such as benzene, naphthalene, chlorobenzene, bromobenzene, methylbenzene, ethylbenzene, methoxybenzene and ethoxybenzene; heterocycles such as an oxazole ring, a benzoxazole ring, an isoxazole ring, a naphthoxazole ring, an indolenine ring, a benzoindolenine ring, a naphthoindolenine ring, an imidazole ring, a benzimidazole ring, a naphthoimidazole ring, a furan ring, a benzofuran ring, a naphthofuran ring, a pyrrole ring, a thiophene ring, a pyridine ring, a pyrrolopyridine ring, a pyrrole ring, an indolidine ring, an indole ring, a quinoline ring, a quinoxaline ring, an imidazoquinoxaline ring, a thiazole ring, a benzothiazole ring and a naphthothiazole ring; aliphatic rings such as cyclopropane, cyclobutane, cyclopentane, cyclohexane, cycloheptane and cyclooctane.

Examples of the cycloalkane-1,1-diyl group having 3 to 6 carbon atoms represented by X and X' may include cyclopropane-1,1-diyl, cyclobutane-1,1-diyl, 2,4-dimethylcyclobutane-1,1-diyl, 3-dimethylcyclobutane-1,1-diyl, cyclopentan-1,1-diyl and cyclohexane-1,1-diyl; and examples of the alkyl group having 1 to 20 carbon atom(s) represented by $R^{51}$ and $R^{52}$ in X and X' may include methyl, ethyl, propyl, isopropyl, butyl, sec-butyl, tert-butyl, isobutyl, amyl, isoamyl, tert-amyl, hexyl, 2-hexyl, 3-hexyl, cyclohexyl, 1-methylcyclohexyl, heptyl, 2-heptyl, 3-heptyl, isoheptyl, tert-heptyl, n-octyl, isooctyl, tert-octyl, 2-ethylhexyl, nonyl, isononyl, decyl, dodecyl, tridecyl, tetradecyl, pentadecyl, hexadecyl, heptadecyl, octadecyl and the like, and any number of the hydrogen atom(s) in these alkyl groups may be substituted with a hydroxyl group, a halogen atom, a cyano group or a nitro group.

Examples of the aryl group having 6 to 30 carbon atoms represented by $R^{51}$ and $R^{52}$ may include the groups exemplified for the explanation of the above-mentioned $R^1$, and any number of the hydrogen atom(s) in these aryl groups may be substituted with a hydroxyl group, a halogen atom, a cyano group or a nitro group.

Examples of the arylalkyl group having 7 to 30 carbon atoms represented by $R^{51}$ and $R^{52}$ may include the groups exemplified for the explanation of the above-mentioned $R^1$, and any number of the hydrogen atom(s) in these arylalkyl group may be substituted with a hydroxyl group, a halogen atom, a cyano group or a nitro group.

Examples of the alkyl group having 1 to 20 carbon atom(s) optionally substituted by a hydroxyl group, a halogen atom, a cyano group or a nitro group, the aryl group having 6 to 30 carbon atoms optionally substituted by a hydroxyl group, a halogen atom, a cyano group or a nitro group, or the arylalkyl group having 7 to 30 carbon atoms optionally substituted by a hydroxyl group, a halogen atom, a cyano group or a nitro group represented by Y, Y' and $Y^2$ may include the groups exemplified in the explanation of the above-mentioned $R^{51}$ and $R^{52}$; and the methylene group(s) in the alkyl groups and arylalkyl groups in these Y, and $Y^2$ may be interrupted by —O—, —S—, —CO—, —COO—, —OCO—, —SO$_2$—, —NH—, —CONH—, —NHCO—, —N=CH— or —CH=CH—. Examples may include alkyl groups such as methyl, ethyl, propyl, isopropyl, butyl, sec-butyl, tert-butyl, isobutyl, amyl, isoamyl, tert-amyl, hexyl, cyclohexyl, cyclohexylmethyl, 2-cyclohexylethyl, heptyl, isoheptyl, tert-heptyl, n-octyl, isooctyl, tert-octyl, 2-ethylhexyl, nonyl, isononyl, decyl, dodecyl, tridecyl, tetradecyl, pentadecyl, hexadecyl, heptadecyl and octadecyl; alkenyl groups such as vinyl, 1-methylethenyl, 2-methylethenyl, propenyl, butenyl, isobutenyl, pentenyl, hexenyl, heptenyl, octenyl, decenyl, pentadecenyl and 1-phenylpropen-3-yl; alkylaryl groups such as phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl) phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl and cyclohexylphenyl; arylalkyl groups such as benzyl, phenetyl, 2-phenylpropane-2-yl, diphenylmethyl, triphenylmethyl, styryl and cinnamyl; and the like, which are interrupted by an ether bond or a thioether bond, such as 2-methoxyethyl, 3-methoxypropyl, 4-methoxybutyl, 2-butoxyethyl, methoxyethoxyethyl, methoxyethoxyethoxyethyl, 3-methoxybutyl, 2-phenoxyethyl, 3-phenoxypropyl, 2-methylthioethyl and 2-phenylthioethyl.

Examples of the halogen atom represented by $R^{O1}$, $R^{O2}$, $R^{O3}$ and $R^{O4}$ in the above-mentioned general formula (11) may include the groups exemplified in the explanation of the above-mentioned $R^1$; and examples of the alkyl group having 1 to 4 carbon atom(s) may include methyl, ethyl, propyl, isopropyl, butyl, sec-butyl, tert-butyl and isobutyl, and any number of the hydrogen atom(s) in these alkyl groups may be substituted with a hydroxyl group, a halogen atom, a cyano group or a nitro group.

Furthermore, examples of the cycloalkene ring formed by bonding of $R^{O1}$ and $R^{O4}$ may include a cyclobutene ring, a cyclopentene ring, a cyclohexene ring and the like, and examples of the hetero ring formed by bonding of $R^{O1}$ and $R^{O4}$ may include a pyrrole ring, a dihydropyrrole ring, a pyridine ring and the like.

In the above-mentioned general formula (12), examples of the halogen atom represented by $R^{O1}$ may include the groups exemplified in the explanation of the above-mentioned $R^1$; and examples of the alkyl group having 1 to 4 carbon atom(s) may include methyl, ethyl, propyl, isopropyl, butyl, sec-butyl, tert-butyl, isobutyl, and any number of the hydrogen atom(s) in these alkyl groups may be substituted with a hydroxyl group, a halogen atom, a cyano group or a nitro group.

Examples of the 5-membered ring including G' and T' optionally including hetero atom(s) may include a cyclopentene ring, a cyclopentadiene ring, a pyrrole ring, an imidazole ring, a pyrazole ring, a triazole ring, a thiophene ring, a furan ring, a thiazole ring, an isothiazole ring, an oxazole ring, an isoxazole ring, a dihydropyrrole ring, a dihydroimidazole ring, a dihydropyrazole ring, a triazole ring, a dihydrothiophene ring, a dihydrofuran ring, a dihydrothiazole ring, a dihydroisothiazole ring, a dihydrooxazole ring, a dihydroisoxazole ring and the like; and examples of the 6-membered ring including G' and T' optionally including hetero atom(s) may include a pyridine ring, a pyrazine ring, a pyrimidine ring, a pyridazine ring, a pyran ring, a thiopyran ring and the like.

Furthermore, these rings including G' and T' may be substituted by a halogen atom such as fluorine, chlorine, bromine and iodine, a nitro group, a cyano group, an alkyl group having 1 to 4 carbon atom(s) such as methyl, ethyl, propyl, isopropyl, butyl, isobutyl, tert-butyl and trifluoromethyl, an alkoxy group having 1 to 4 carbon atom(s) such as methoxy, ethoxy, propoxy, isopropoxy, butoxy, sec-butoxy, tert-butoxy and trifluoromethyloxy.

Among the squarylium compounds represented by the above-mentioned general formula (1), those represented by the following general formula (2) are preferable since they are excellent in absorption wavelength and light resistance and useful as a color tone correcting agent, and those represented by the following general formula (3) are more preferable since the production cost therefor is low.

[Chemical Formula 6]

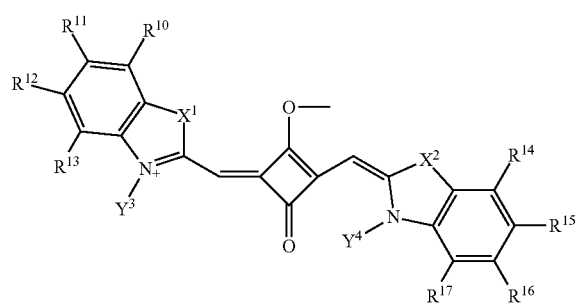

(2)

wherein
at least one of $R^{10}$ to $R^{13}$ is a nitro group, an alkyl group having 1 to 4 carbon atom(s), a halogen-substituted alkyl group having 1 to 4 carbon atom(s), an alkoxy group having 1 to 4 carbon atom(s) or a halogen-substituted alkoxy group having 1 to 4 carbon atom(s), and other is/are each a hydrogen atom,
at least one of $R^{14}$ to $R^{17}$ is a nitro group, an alkyl group having 1 to 4 carbon atom(s), a halogen-substituted alkyl group having 1 to 4 carbon atom(s), an alkoxy group having 1 to 4 carbon atom(s) or a halogen-substituted alkoxy group having 1 to 4 carbon atom(s), and other is/are each a hydrogen atom, $X^1$ and $X^2$ each represents an oxygen atom, a sulfur atom, a serenium atom, —$CR^{53}R^{54}$— or a cycloalkane-1,1-diyl group having 3 to 6 carbon atoms, wherein $R^{53}$ and $R^{54}$ each represents a group represented by the general formula (11) or (12), an alkyl group having 1 to 20 carbon atom(s) optionally substituted by a hydroxyl group, a halogen atom, a cyano group or a nitro group, an aryl group having 6 to 30 carbon atoms optionally substituted by a hydroxyl group, a halogen atom, a cyano group or a nitro group, or an arylalkyl group having 7 to 30 carbon atoms optionally substituted by a hydroxyl group, a halogen atom, a cyano group or a nitro group, and $Y^3$ and $Y^4$ each represents a group that is similar to Y.

In the above-mentioned general formula (2), examples of the alkyl group having 1 to 4 carbon atom(s) represented by $R^{10}$ to $R^{13}$ and $R^{14}$ to $R^{17}$ may include methyl, ethyl, propyl, isopropyl, butyl, sec-butyl, tert-butyl and isobutyl;

examples of the halogen-substituted alkyl group having 1 to 4 carbon atom(s) may include chloromethyl, dichloromethyl, trichloromethyl, fluoromethyl, fluoromethyl, trifluoromethyl, nonafluorobutyl and the like;

examples of the alkoxy group having 1 to 4 carbon atom(s) may include methyloxy, ethyloxy, propyloxy, isopropyloxy, butyloxy, sec-butyloxy, tert-butyloxy and isobutyloxy;

examples of the halogen-substituted alkoxy group having 1 to 4 carbon atom(s) may include chloromethyloxy, dichloromethyloxy, trichloromethyloxy, fluoromethyloxy, fluoromethyloxy, trifluoromethyloxy, nonafluorobutyloxy and the like.

Furthermore, examples of the alkyl group having 1 to 20 carbon atom(s) optionally substituted by a hydroxyl group, a halogen atom, a cyano group or a nitro group, the aryl group having 6 to 30 carbon atom(s) optionally substituted by a hydroxyl group, a halogen atom, a cyano group or a nitro group and the arylalkyl group having 7 to 30 carbon atoms optionally substituted by a hydroxyl group, a halogen atom, a cyano group or a nitro group represented by $R^{53}$ and $R^{54}$ in $X^1$ and $X^2$ may include the groups the exemplified in the explanation of the above-mentioned $R^{51}$ and $R^{52}$.

[Chemical Formula 7]

(3)

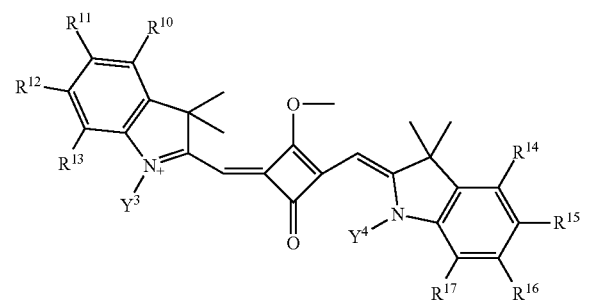

wherein
at least one of $R^{10}$ to $R^{13}$ is a nitro group, a trifluoromethane group or a methoxy group and other is/are each a hydrogen atom, at least one of $R^{14}$ to $R^{17}$ is a nitro group or a trifluoromethane group and other is/are each a hydrogen atom, and $Y^3$ and $Y^4$ each represents a group that is similar to Y.

Specific examples of the squarylium compound represented by the above-mentioned general formula (3) may include the following compounds Nos. 1 to 36.

[Chemical Formula 8]

Compound No. 1

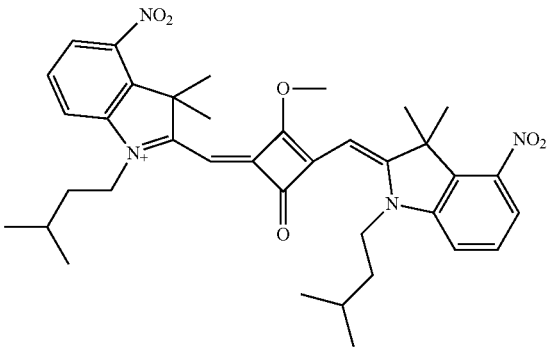

Compound No. 2

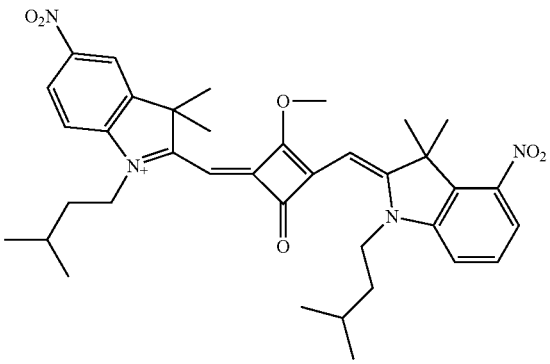

Compound No. 3

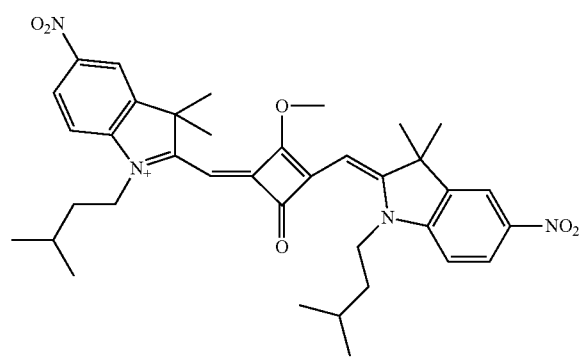

Compound No. 4

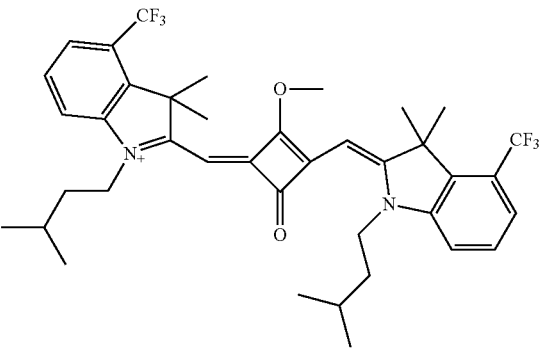

Compound No. 5
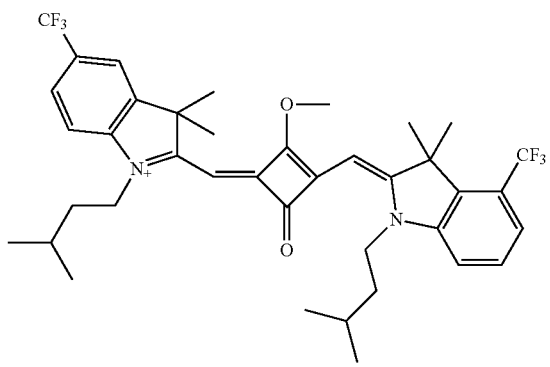
Compound No. 6
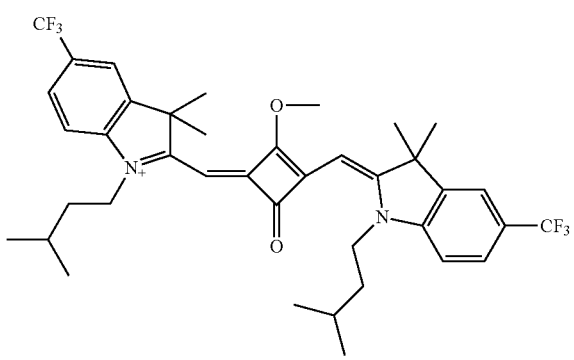
[Chemical Formula 9]
Compound No. 7
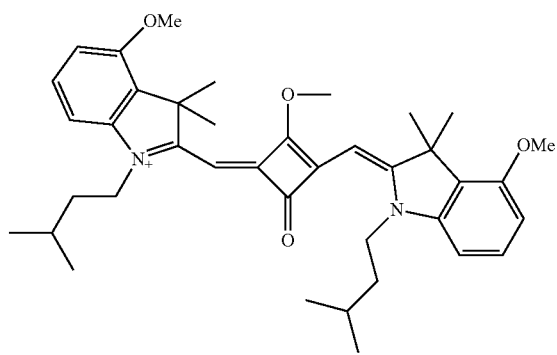
Compound No. 8
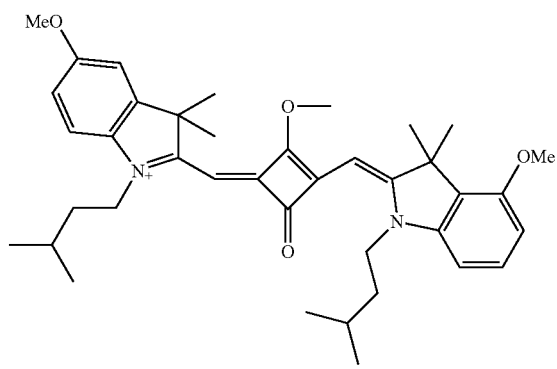
Compound No. 9
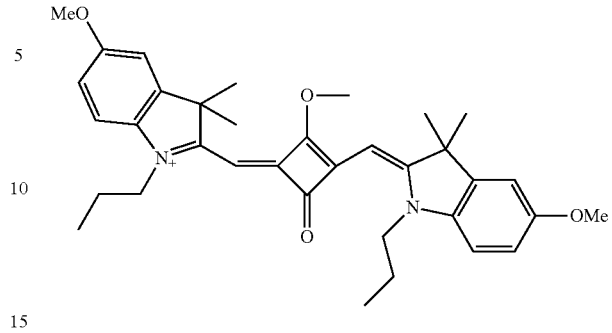
Compound No. 10
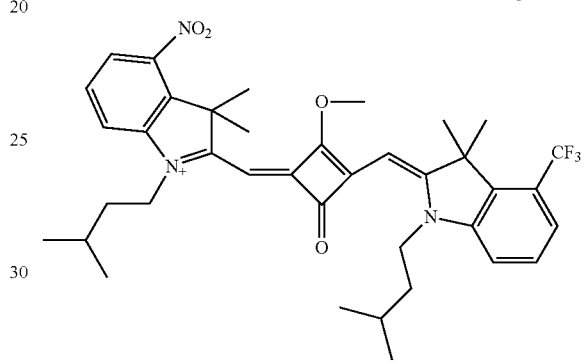
Compound No. 11
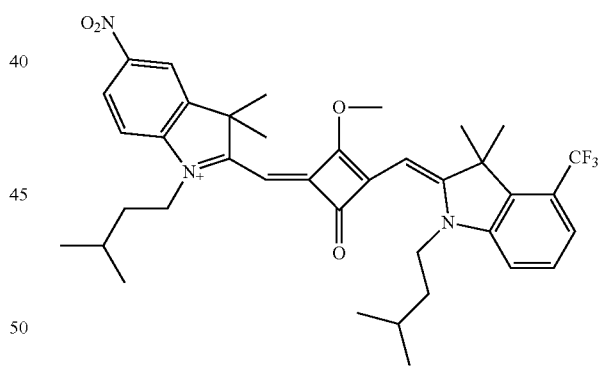
Compound No. 12
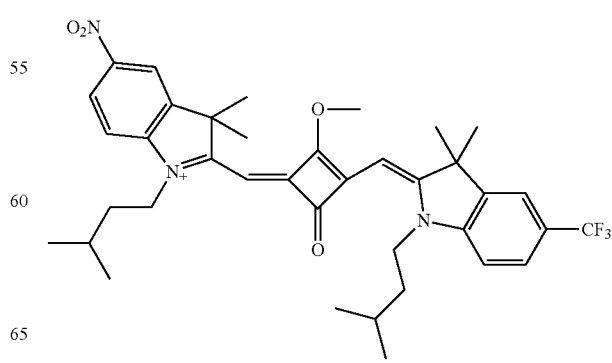

-continued
[Chemical Formula 10]
Compound No. 13
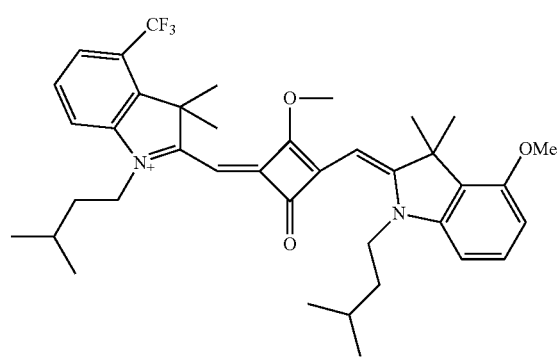
Compound No. 14
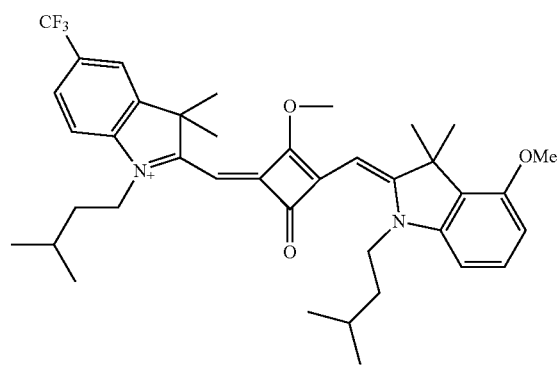
Compound No. 15
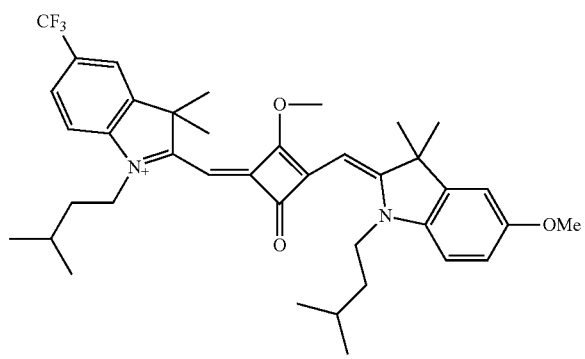
Compound No. 16
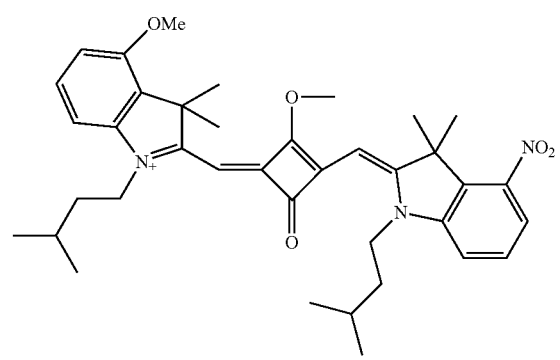
Compound No. 17
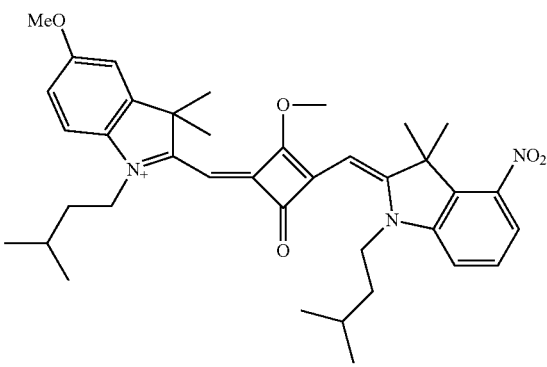
Compound No. 18
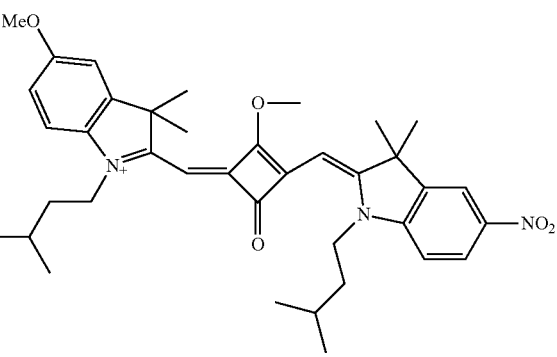
[Chemical Formula 11]
Compound No. 19
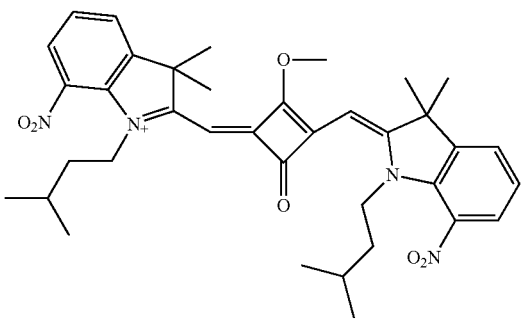
Compound No. 20
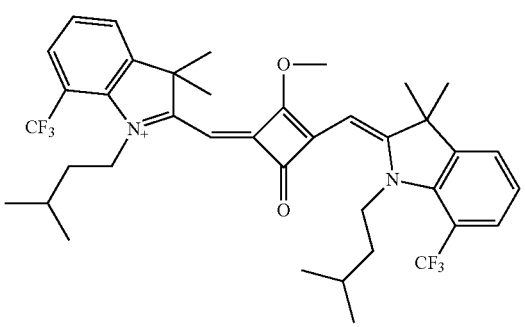

Compound No. 21
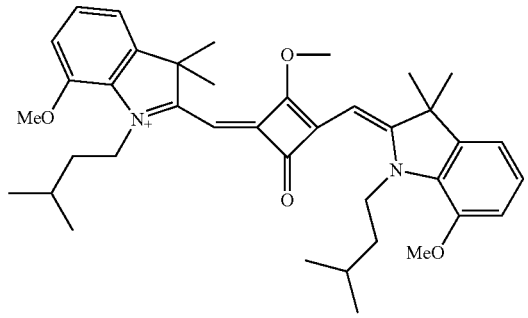
Compound No. 22
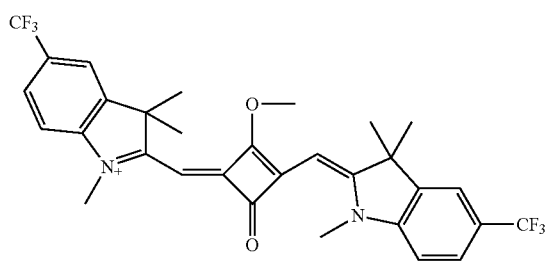
Compound No. 23
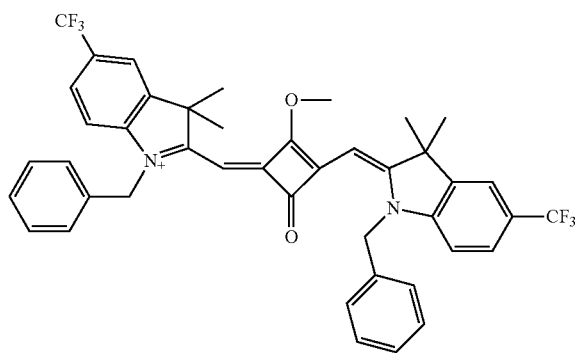
Compound No. 24
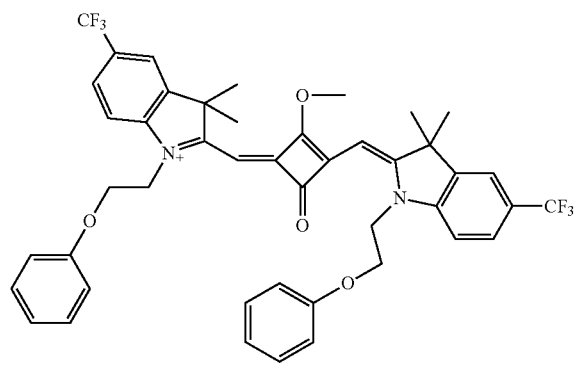
[Chemical Formula 12]
Compound No. 25
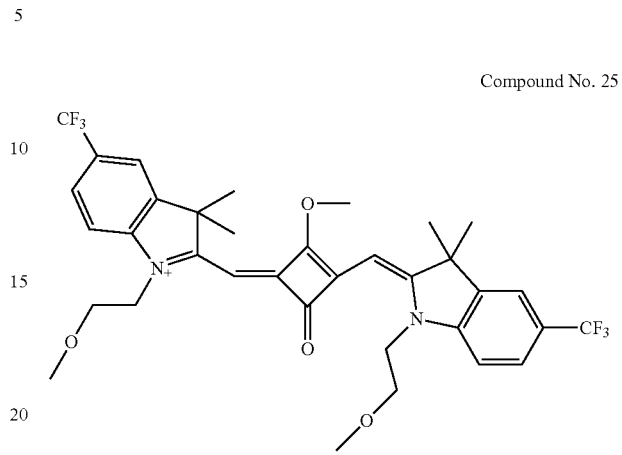
Compound No. 26
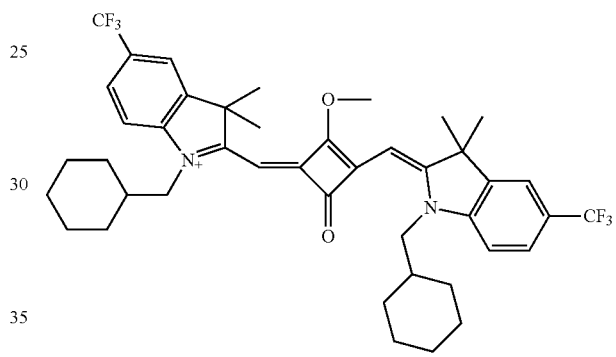
Compound No. 27
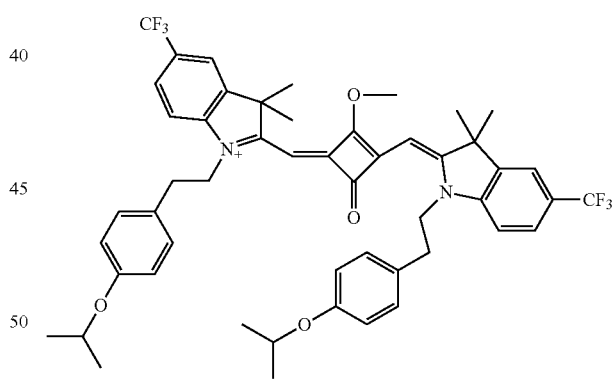
Compound No. 28
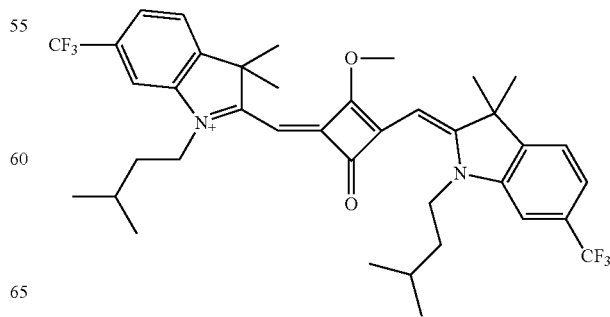

Compound No. 29

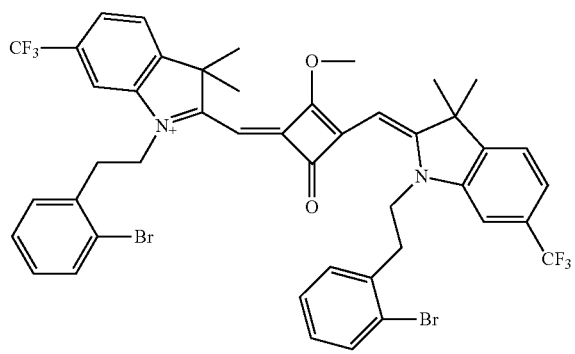

Compound No. 30

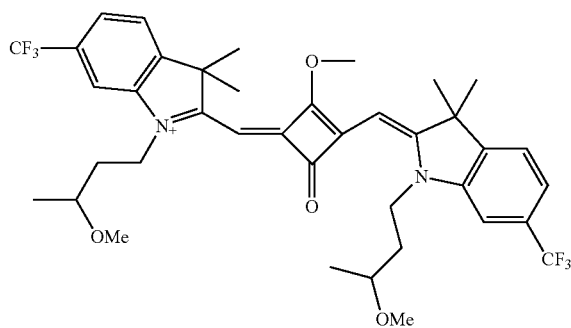

[Chemical Formula 13]

Compound No. 31

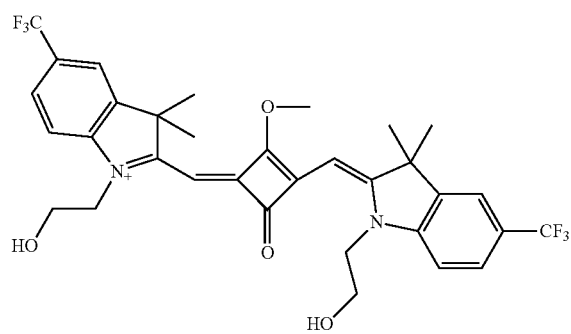

Compound No. 32

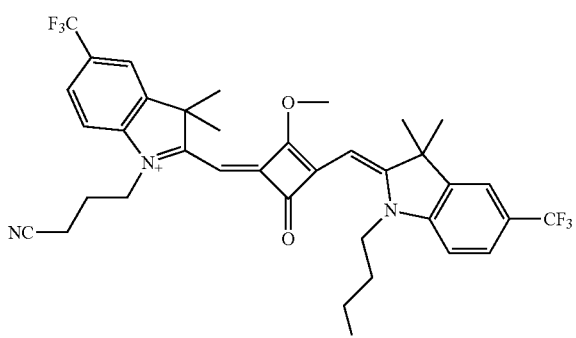

Compound No. 33

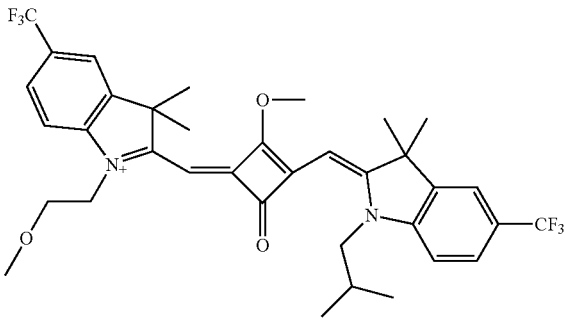

Compound No. 34

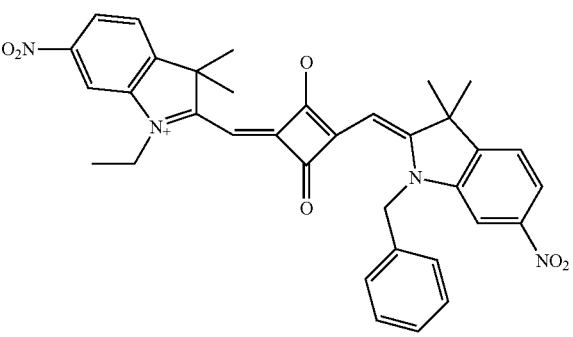

Compound No. 35

Compound No. 36

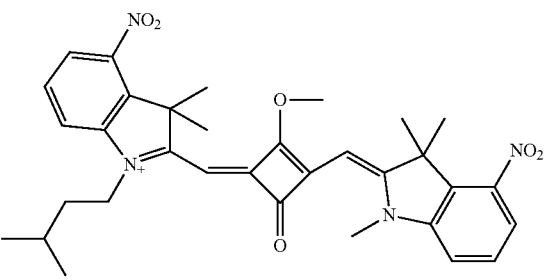

Furthermore, among the compounds represented by the above-mentioned general formula (3), the novel squarylium compound of the present invention represented by the following general formula (4) is even more preferable since the production cost therefor is further decreased.

[Chemical Formula 14]

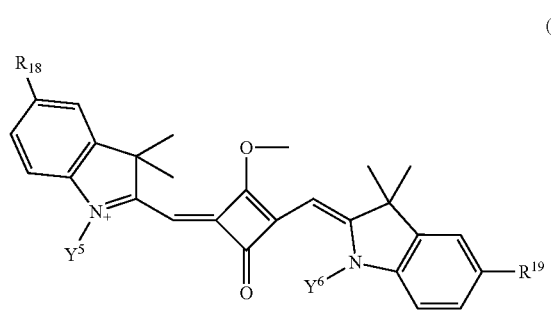

(4)

wherein $R^{18}$ and $R^{19}$ each represents a nitro group, a trifluoromethane group or a methoxy group, and $Y^5$ and $Y^6$ each represents an alkyl group having 1 to 18 carbon atom(s), an ether group having 3 to 18 carbon atoms, an aryl group having 6 to 18 carbon atoms or an arylalkyl group having 7 to 18 carbon atoms.

Examples of the alkyl group having 1 to 18 carbon atom(s) represented by $Y^5$ and $Y^6$ may include methyl, ethyl, propyl, isopropyl, butyl, sec-butyl, tert-butyl, isobutyl, amyl, isoamyl, tert-amyl, hexyl, 2-hexyl, 3-hexyl, cyclohexyl, 1-methylcyclohexyl, heptyl, 2-heptyl, 3-heptyl, isoheptyl, tert-heptyl, 1-octyl, isooctyl, tert-octyl, nonyl, isononyl, decyl, dodecyl, tridecyl, tetradecyl, pentadecyl, hexadecyl, heptadecyl, octadecyl and the like;

examples of the ether group having 3 to 18 carbon atoms may include 2-methoxyethyl, 2-(2-methoxy)ethoxyethyl, 2-ethoxyethyl, 2-butoxyethyl, 4-methoxybutyl, 3-methoxybutyl, 2-phenoxyethyl and the like;

examples of the aryl group having 6 to 18 carbon atoms may include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-ditert-butylphenyl, 2,5-ditert-butylphenyl, 2,6-di-tert-butylphenyl, 2,4-ditert-pentylphenyl, 2,5-ditert-amylphenyl, cyclohexylphenyl, biphenyl and 2,4,5-trimethylphenyl; and examples of the arylalkyl group having 7 to 30 carbon atoms may include benzyl, phenetyl, 2-phenylpropane-2-yl, diphenylmethyl, triphenylmethyl, styryl, cinnamyl and the like.

Examples of the specific compounds that correspond to the squarylium compound represented by the above-mentioned general formula (4) may include the above-mentioned compounds Nos. 3, 6, 9, 12, 15, 18, 22, 23, 24, 25, 26, 33 and 35.

The squarylium compound of the present invention represented by the above-mentioned general formula (4) is not specifically limited by its production method, and can be obtained by utilizing a well-known general reaction. For example, it can be synthesized by a dehydration reaction between squaric acid and an indolium compound, or a reaction between a squaric acid alkyl ester and an indolium compound. In order to promote these reactions, an inorganic base such as sodium hydroxide or an organic base such as triethylamine can suitably be used. Specifically, it can be produced according to the following synthetic route.

[Chemical Formula 15]

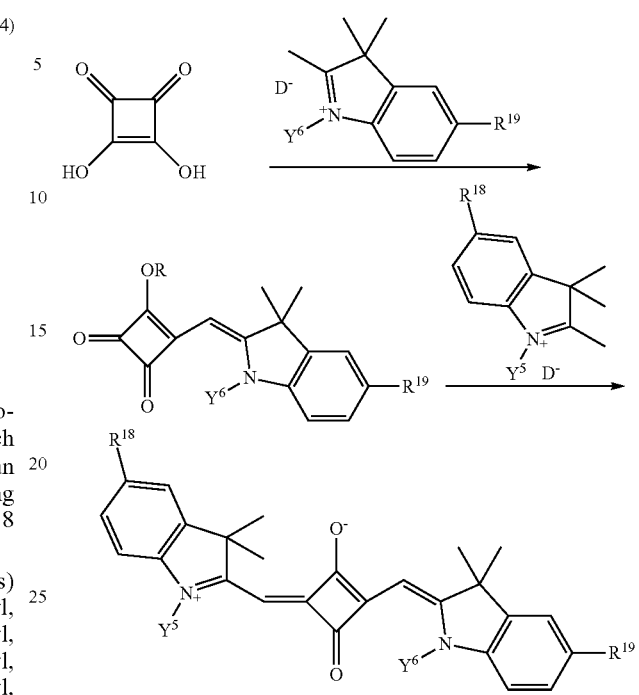

wherein in the reaction formula, $R^{18}$, $R^{19}$, $Y^5$ and $Y^6$ have the same meanings as those defined for the general formula (4), $D^-$ represents a counterion.

Examples of the counterion represented by $D^-$ in the above-mentioned reaction formula may include halogen anions such as a chlorine anion, a bromine anion, an iodine anion and a fluorine anion; inorganic-based anions such as a perchlorate anion, a chlorate, a thiocyanate anion, a hexafluorophosphate anion, a hexafluoroantimony anion and a tetrafluoroborate anion; organic sulfonyloxy ions such as a benzenesulfonate anion, a toluenesulfonate anion and a trifluoromethanesulfonate anion.

Not only the squarylium compound of the present invention represented by the above-mentioned general formula (4) but also the squarylium compounds represented by the above-mentioned formulas (1) to (3) can be produced by a similar method.

The squarylium compound of the present invention is suitably used as a color tone correcting agent for the optical filter mentioned below, and also used as optical elements such as colorants for optical recording materials, dye-sensitized solar cells, optical electrochemical cells, nonlinear optical apparatuses, elecrochromic displays, holograms, organic semiconductors, organic ELs, photosensitive materials for silver halide photography, photosensitizers, print inks, inkjets, color toners for electrophotography, cosmetics, plastics and the like; and dyes for dyes for stains for proteins and detection of substances.

Next, the optical filter of the present invention is explained.

The optical filter of the present invention includes at least one kind of the above-mentioned color tone correcting agents of the present invention. The color tone correcting agents each has an absorption maximum wavelength within the range from 500 to 800 nm or in the vicinity thereof and can selectively absorb and interrupt visible ray, and thus the optical filter of the present invention including the color tone correcting agent is specifically preferable as an optical filter for an image display apparatus used for improving the quality of displayed images and an optical filter display for an illumination apparatus. Furthermore, the optical filter of the present invention can also be used in various uses such as lenses for glasses, windows, uses in analysis devices, uses in semiconductor devices, uses in astronomical observation and uses in optical communication.

In the optical filter of the present invention, the content of the squarylium compound represented by the above-mentioned general formula (1) is generally from 0.1 to 10,000 mg/m$^2$, preferably from 5 to 1,000 mg/m$^2$ in total. When the content is lower than 0.1 mg/m$^2$, light absorption effect cannot be exerted sufficiently, and when the compound is included by exceeding 10,000 mg/m$^2$, the color tone of the filter may become too strong to decrease display quality and the like, and brightness may decrease due to increase in the incorporation amount of a light absorber.

Although the form of the optical filter of the present invention is not specifically limited, a form including a transparent substrate, and optionally including various layers such as a primer layer, an antireflective layer, a hard coat layer, a lubricating layer and a protective layer is generally exemplified. Examples of a method for incorporating the color tone correcting agent of the present invention, and optional components such as a light absorber including a pigment compound other than the color tone correcting agent of the present invention and various stabilizers, which are used as necessary, in the optical filter of the present invention may include (1) a method including incorporating into the transparent substrate or optional layers, (2) a method including coating on the transparent substrate or optional layers, (3) a method including incorporating into pressure-sensitive adhesive layers of the adjacent two layers selected from the transparent substrate and optional layers, (4) a method including providing, besides the optional layers, a light absorption layer including a light absorber such as the color tone correcting agent of the present invention, and (5) a method including directly incorporating into a resin composition that forms the transparent substrate, and processing by using this to give a desired form such as a film and an optical element.

Examples of the material for the above-mentioned transparent substrate may include inorganic materials such as glass, and polymer materials including cellulose esters such as diacetyl cellulose, triacetyl cellulose (TAC), propionyl cellulose, butyryl cellulose, acetylpropionyl cellulose and nitrocellulose; polyamides; polycarbonates; polyesters such as polyethylene telephthalate, polyethylene naphthalate, polybutylene telephthalate, poly-1,4-cyclohexanedimethylene telephthalate, polyethylene-1,2-diphenoxyethane-4,4'-dicarboxylate and polybutylene telephthalate; polystyrenes; polyolefins such as polyethylene, polypropylene and polymethylpentene; acrylic-based resins such as polymethyl methacrylate; polycarbonates; polysulfones; polyethersulfones; polyetherketones; polyetherimides; polyoxyethylene; and norbornene resins. The transparent substrate has a transmittance of, preferably 80% or more, more preferably 86% or more. The transparent substrate has a haze of, preferably 2% or less, more preferably 1% or less. It preferably has a refractive index of from 1.45 to 1.70.

Other light absorbers other than the color tone correcting agent of the present invention, infrared ray absorbers, ultraviolet absorbers, fluorescence quenchers, antioxidants such as phenol-based, phosphorous-based and sulfur-based antioxidants, flame retardants, lubricants, antistatic agents, inorganic microparticles, agents for imparting light resistance, aromatic nitroso compounds, aminium compounds, iminium compounds, transition metal chelate compounds, viscose minerals and the like can be added to the above-mentioned transparent substrate, and the above-mentioned transparent substrate can be subjected to various surface treatments.

Examples of the light absorber other than the above-mentioned color tone correcting agent of the present invention may include light absorbers for color tone adjustment and light absorbers for preventing reflection and background reflection of exterior light when the optical filter is used in an image display apparatus, and may specifically include light absorbers for preventing malfunction of an infrared remote control when the image display apparatus is a plasma display.

Examples of the above-mentioned light absorber for color tone adjustment may include those used for removing orange light at a wavelength of from 450 to 620 nm such as trimethine cyanine derivatives such as trimethineindolium compounds, trimethinebenzoxazolium compounds and trimethinebenzothiazolium compounds; pentamethinecyanine derivatives such as pentamethineoxazolium compounds and pentamethinethiazolium compounds; squarylium pigment derivatives other than the color tone correcting agent of the present invention; azomethine pigment derivatives; xanthene pigment derivatives; azo pigment derivatives; oxonol pigment derivatives; benzylidene pigment derivative; pyrromethene pigment derivatives; azo metal complex derivatives: rhodamine pigment derivatives; phthalocyanine derivatives; porphyrin derivatives; dipyrromethene metal chelate compounds and the like.

Examples of the above-mentioned light absorbers for preventing reflection and background reflection of exterior light (which corresponds to a wavelength of from 480 to 500 nm) may include trimethinecyanine derivatives such as trimethineindolium compounds, trimethineoxazolium compounds, trimethinethiazolium compounds and indolidenetrimethine thiazonium compounds; phthalocyanine derivatives; naphthalocyanine derivatives; porphyrin derivatives; dipyrromethene metal chelate compounds; and the like.

Examples of the above-mentioned light absorbers for preventing malfunction of an infrared remote control (which corresponds to a wavelength of from 750 to 1,100 nm) may include diimonium compounds; pentamethinecyanine derivatives such as pentamethinebenzoindolium compounds, pentamethinebenzoxazolium compounds and pentamethinebenzothiazolium compounds; heptamethinecyanine derivatives such as heptamethineindolium compounds, heptamethinebenzoindolium compounds, heptamethineoxazolium compounds, heptamethinebenzoxazolium compounds, heptamethinethiazolium compounds and heptamethinebenzothiazolium compounds; squarylium derivatives; nickel complexes such as bis(stilbenedithiolato) compounds, bis (benzenedithiolato)nickel compounds and bis(camphordithiolato)nickel compounds; squarylium derivatives; azo pigment derivatives; phthalocyanine derivatives; porphyrin derivatives; dipyrromethene metal chelate compounds; and the like.

In the optical filter of the present invention, the above-mentioned light absorbers for color tone adjustment, light absorbers for preventing reflection and background reflection of exterior light and light absorbers for preventing malfunction of an infrared remote control (near-infrared ray absorber) may be incorporated in the same layer as the layer including the color tone correcting agent of the present invention, or may be incorporated in other layer. The use amounts thereof are each in the range of generally from 0.1 to 1,000 mg/m$^2$, preferably from 5 to 100 mg/m$^2$, per a unit area of the optical filter.

Furthermore, examples of the above-mentioned inorganic microparticles that can be added to the above-mentioned transparent substrate may include silicon dioxide, titanium dioxide, barium sulfate, calcium carbonate, talc, kaolin and the like.

Examples of the above-mentioned various surface treatments to which the above-mentioned transparent substrate can be subjected may include a treatment with a chemical agent, a mechanical treatment, a corona discharge treatment, a flame treatment, an UV irradiation treatment, a high-frequency wave treatment, a glow discharge treatment, an active plasma treatment, a laser treatment, a treatment with a mixed acid, an ozone oxidation treatment and the like.

The above-mentioned primer layer that can be provided to the optical filter of the present invention is a layer used between the transparent substrate and optical filter layer when a filter layer including a light absorber is provided besides the optional layers. The above-mentioned primer layer is formed as a layer including a layer including a polymer having a glass transition temperature of from −60 to 60° C., a layer having a rough surface at the side of the filter layer, or a layer including a polymer having affinity with the polymer in the filter layer. Alternatively, the primer layer may be provided on the surface on which the filter layer is not provided of the transparent substrate so as to improve the adhesion force between the transparent substrate and the layer provided thereon (for example, an antireflective layer, a hard coat layer), or may be provided so as to improve the affinity between an adhesive for adhering the optical filter and image display apparatus and the optical filter. The primer layer has a thickness of, preferably from 2 nm to 20 μm, more preferably from 5 nm to 5 μm, further preferably from 20 nm to 2 μm, even more preferably from 50 nm to 1 μm, and the most preferably from 80 nm to 300 nm. The primer layer including a polymer having a glass transition temperature of from −60 to 60° C. attaches the transparent substrate to the filter layer by the adherability of the polymer. The polymer having a glass transition temperature of from −60 to 60° C. can be obtained by, for example, polymerization of vinyl chloride, vinylidene chloride, vinyl acetate, butadiene, neoprene, styrene, chloroprene, acrylic acid ester, methacrylic acid ester, acrylonitrile or methyl vinyl ether, or copolymerization thereof. The glass transition temperature is preferably 50° C. or less, more preferably 40° C. or less, further preferably 30° C. or less, even further preferably 25° C. or less, and the most preferably 20° C. or less. The primer layer has an elastic rate at 25° C. of preferably from 1 to 1,000 MPa, further preferably from 5 to 800 MPa, and the most preferably from 10 to 500 MPa. The primer layer having a rough surface on the surface of the filter attaches the transparent substrate to the filter layer by forming the filter layer on the rough surface. The primer layer having a rough surface on the surface of the filter layer can be readily formed by applying a polymer latex. The latex has an average particle size of preferably from 0.02 to 3 μm, more preferably from 0.05 to 1 μm. Examples of the polymer having affinity with the binder polymer in the filter layer may include acryl resins, cellulose derivatives, alginic acid, gelatin, casein, starch, polyvinyl alcohols, polyvinyl butyral, polyvinyl pyrrolidone, soluble nylons, polymer latexes and the like. Alternatively, two or more primer layers may be provided to the optical filter of the present invention. The primer layer may include a solvent for swelling the transparent substrate, a matting agent, a surfactant, an antistatic agent, a coating aid, a film-curing agent and the like.

In the above-mentioned antireflective layer that can be provided to the optical filter of the present invention, a low refractive index layer is essential. The low refractive index layer has a lower refractive index than the refractive index of the above-mentioned transparent substrate. The low refractive index layer has a refractive index of preferably from 1.20 to 1.55, more preferably from 1.30 to 1.50. The low refractive index layer has a thickness of preferably from 50 to 400 nm, more preferably from 50 to 200 nm. The low refractive index layer can be formed as a layer including a fluorine-containing polymer, which has a low refractive index (described in each of JP-A Nos. 57-34526, 3-130103, 6-115023, 8-313702 and 7-168004), a layer obtained by a sol-gel process (described in each of JP-A Nos. 5-208811, 6-299091 and 7-168003), or a layer including microparticles (described in each of Japanese Patent Application Publication No. 60-59250, and JP-A Nos. 5-13021, 6-56478, 7-92306 and 9-288201). In the layer including microparticles, voids can be formed as microvoids between the microparticles or in the microparticles in the low refractive index layer. The layer including microparticles preferably has a porosity of from 3 to 50% by volume, and more preferably has a porosity of from 5 to 35% by volume.

In order to prevent reflection in a wide wavelength area, it is preferable to laminate a layer having a high refractive index (a middle or high refractive index layer) besides the low refractive index layer in the above-mentioned antireflective layer. The high refractive index layer has a refractive index of preferably from 1.65 to 2.40, more preferably from 1.70 to 2.20. The refractive index of the middle refractive index layer is adjusted so as to be intermediate in value between the refractive index of the low refractive index layer and the refractive index of the high refractive index layer. The middle refractive index layer has a refractive index of preferably from 1.50 to 1.90, more preferably from 1.55 to 1.70. The middle or high refractive index layer has a thickness of preferably from 5 nm to 100 μm, more preferably from 10 nm to 10 μm, and the most preferably from 30 nm to 1 μM. The middle or high refractive index layer has a haze of preferably 5% or less, more preferably 3% or less, and the most preferably 1% or less. The middle or high refractive index layer can be formed by using a polymer binder having a relatively high refractive index. Examples of the polymer having a high refractive index may include polystyrenes, styrene copolymers, styrene-butadiene copolymers, polyvinyl chloride, polycarbonates, polyamides, melamine resins, phenol resins, epoxy resins, polyurethanes obtained by a reaction of a cyclic (arycyclic or aromatic) isocyanate and a polyol, and the like. Polymers having other cyclic (aromatic, heterocyclic, arycyclic) groups and polymers having halogen atoms other than fluorine as substituents also have a high refractive index. A polymer formed by a polymerization reaction of a monomer to which a double bond has been introduced to enable radical curing may also be used.

In order to obtain a higher refractive index, inorganic microparticles may be dispersed in the above-mentioned polymer binder. The inorganic microparticles has a refractive index of preferably from 1.80 to 2.80. The inorganic microparticles are preferably formed from an oxide or sulfide of a metal. Examples of the oxide or sulfide of a metal may include titanium oxides (for example, rutile, mixed crystals of rutile/anatase, anatase, amorphous structure), tin oxide, indium oxide, zinc oxide, zirconium oxide, zinc sulfide and the like. Among these, titanium oxide, tin oxide and indium oxide are specifically preferable. The inorganic microparticles can include the oxide or sulfide of these metals as a major component, and can further include other element. The major component means a component having the largest content (% by mass %) among the components that constitute the particles. Examples of other element may include Ti, Zr, Sn, Sb, Cu, Fe, Mn, Pb, Cd, As, Cr, Hg, Zn, Al, Mg, Si, P, S and the like. The middle or high refractive index layer can also be formed by using an inorganic material having film-forming property, which can be dispersed in a solvent or the inorganic material itself is a liquid, such as alkoxides of various elements, a salt of an organic salt, a coordinated compound bound to a coordinatable compound (for example, a chelate compound) and an active inorganic polymer.

An anti-glare function (a function for scattering incident light on a surface to prevent transfer of the background around a film on the surface of the film) can be imparted to the surface of the above-mentioned antireflective layer. For example, the antireflective layer having an anti-glare function can be obtained by forming fine asperity on the surface of the transparent film and forming the antireflective layer on the surface thereof, or by forming the antireflective layer, and thereafter forming asperity on the surface by an emboss roll. The antireflective layer having an anti-glare function generally has a haze of from 3 to 30%.

The above-mentioned hard coat layer that can be provided to the optical filter of the present invention has a higher hardness than the hardness of the above-mentioned transparent substrate. The hard coat layer preferably includes a crosslinked polymer. The hard coat layer can be formed by using an acryl-based, urethane-based or epoxy-based polymer, oligomer or monomer (for example, an ultraviolet-curable resin) and the like. The hard coat layer can also be formed from a silica-based material.

A lubricating layer may be formed on the surface of the above-mentioned antireflective layer (low refractive index layer). The lubricating layer has a function to impart slipping property to the surface of the low refractive index layer to improve scratch resistance. The lubricating layer can be formed by using a polyorganosiloxane (for example, a silicon oil), a natural wax, a petroleum wax, a higher aliphatic acid metal salt or a fluorine-based lubricant, or a derivative thereof. The lubricating layer preferably has a thickness of from 2 to 20 nm.

During incorporation of the color tone correcting agent of the present invention in the optical filter, in the case when the above-mentioned "(3) method including incorporating into the pressure-sensitive adhesive layer between the adjacent two layers selected from the transparent substrate and optional layers" is adopted, it is only necessary to incorporate the color tone correcting agent of the present invention and the like in the pressure-sensitive adhesive, and to attach the adjacent two layers among the above-mentioned transparent substrate and the optional layers by using the pressure-sensitive adhesive. As the pressure-sensitive adhesive, silicone-based, urethane-based, acryl-based pressure-sensitive adhesives, and known transparent adhesives for laminated glass such as polyvinyl butyral adhesives and ethylene-vinyl acetate-based adhesives can be used. Furthermore, in the case when the pressure-sensitive adhesive is used, a crosslinking agent such as metal chelate based, isocyanate-based, epoxy-based crosslinking agents can be used as a curing agent as necessary. Furthermore, the thickness of the pressure-sensitive adhesive layer is preferably adjusted to from 2 to 400 μm.

In the case when the above-mentioned "(4) method including providing, besides the optional layers, a light absorption layer including a light absorber such as the color tone correcting agent of the present invention" is adopted, the color tone correcting agent of the present invention can be used as it is to form a light absorption layer, or can be dispersed in a binder to form a light absorption layer. As the binder, for example, natural polymer materials such as gelatin, casein, starch, cellulose derivatives and alginic acid, or synthetic polymer materials such as polymethyl methacrylate, polyvinyl butyral, polyvinyl pyrrolidone, polyvinyl alcohol, polyvinyl chloride, styrene-butadiene copolymers, polystyrenes, polycarbonates and polyamides are used.

When the above-mentioned binder is used, an organic solvent can simultaneously be used, and the organic solvent is not specifically limited and known various solvent can suitably be used; examples may include alcohols such as isopropanol; ether alcohols such as methyl cellosolve, ethyl cellosolve, butyl cellosolve and butyl diglycol; ketones such as acetone, methyl ethyl ketone, methyl isobutyl ketone, cyclohexanone and diacetone alcohol; esters such as ethyl acetate, butyl acetate and methoxyethyl acetate; acrylic acid esters such as ethyl acrylate and butyl acrylate; fluoroalcohols such as 2,2,3,3-tetrafluoropropanol; hydrocarbons such as hexane, benzene, toluene and xylene; chlorinated hydrocarbons such as methylene dichloride, dichloroethane and chloroform; and the like. These organic solvents can be used solely or as a mixture.

Furthermore, the above-mentioned primer layer, antireflective layer, hard coat layer, lubricating layer, protective layer and the like can be formed by a general coating process. Examples of the coating process may include a dip coating process, an air knife coating process, a curtain coating process, a roller coating process, a wire bar coating process, a gravure coating process, an extrusion coating process using a hopper (this is described in the specification of U.S. Pat. No. 2,681,294) and the like. Two or more layers may be formed by simultaneous coating. The process for the simultaneous coating is described in each of the specifications of U.S. Pat. Nos. 2,761,791, 2,941,898, 3,508,947 and 3,526,528, and in Yuji Harasaki, "Coating Engineering", p. 253 (published by Asakura Shoten, 1973).

In the case when the optical filter of the present invention is prepared by the above-mentioned coating process, the coating solution including the color tone correcting agent of the present invention, an organic solvent and other various additives and the like preferably has a concentration of from 1 to 5% by mass %, specifically from 2 to 3% by mass %.

In the case when the above-mentioned "(5) method including directly incorporating into a resin composition that forms the transparent substrate, and processing by using this to give a desired form such as a film and an optical element" is adopted, the color tone correcting agent of the present invention and the like may be mixed in pellets of a thermoplastic resin composition in advance, or may be added to a thermoplastic resin when the film or the like is mold-processed. Examples of such thermoplastic resin may include polycarbonates, polyethylene telephthalate, polystyrenes, polymethyl methacrylate, norbornene resins, polycycloolefins and the like.

In the case when the optical filter of the present invention is used as an optical filter for an image display apparatus, it is generally disposed on the front surface of the display. For example, the optical filter of the present invention may be directly attached to the surface of the display; in the case when a front board is disposed in front of the display, the optical filter may be attached to the front side (outer side) or rear side (display side) of the front board.

When the optical filter of the present invention is used as an apparatus for an illumination apparatus, it is generally disposed on the side of a light outputting surface of a light guide plate; alternatively, the optical filter may be disposed between a light pipe for inputting light to the light guide plate and the light guide plate, or may be disposed between a light source LED and the light pipe.

EXAMPLES

Hereinafter the present invention will be explained in more detail with referring to the Examples and Evaluation Examples. However, the present invention is not construed to be limited by the following Examples and the like.

Examples 1 to 3 show the synthesis examples of the squarylium compound of the present invention, and Example 4 shows the production example of the optical filter including the color tone correcting agent of the present invention.

Evaluation Example 1 shows the evaluation of the optical property and heat resistance of the squarylium compound of the present invention; Evaluation Example 2 shows the evaluation of the heat resistance of the optical filter of the present invention; and Evaluation Example 3 shows the evaluation of the light resistance of the optical filter of the present invention.

Example 1

Synthesis of Compound No. 3

2.1 parts by mol of 2,2,3-trimethyl-1-(3-methyl-1-butyl)-5-nitro-3H-indolium perchlorate was dispersed in toluene, an aqueous solution of 2.1 parts by mol of sodium hydroxide was added thereto, and a reaction was conducted at room temperature for 2 hours. Thereafter oil-water separation was conducted, the obtained toluene phase was washed with water, 1 part by mol of squaric acid was added thereto, butanol was added thereto so that the mass ratio of the toluene and butanol became 1:4, and a reaction was conducted for 3 hours while stirring was conducted at a temperature of 110° C. and the generated water was removed. The crystal precipitated during the reaction was separated by filtration and dried at 120° C. under a reduced pressure to give the objective product Compound No. 3 at a yield of 76.6%. The results of analyses for the obtained compound were as shown below.
<Results of Analyses>
($^1$H-NMR) Deuterated chloroform solvent
1.07 (d, 12), 1.66 (dt, 4), 1.78 (dtt, 2), 1.83 (s, 12), 4.03 (m, 4), 6.14 (s, 2), 7.02 (d, 2), 8.20 (s, 2), 8.30 (d, 2)
(TG) Amount of sample: 2.33 mg, measurement conditions: $N_2$; 200 ml/min, temperature raising; 10° C./min, weight loss initiation temperature; 311° C.

Example 2

Synthesis of Compound No. 6

2.1 parts by mol of 2,2,3-trimethyl-1-(3-methyl-1-butyl)-5-trifluoromethyl-3H-indolium tosylate and 1 part by mol of squaric acid were added to a mixed solvent including toluene and butanol at a mass ratio of 1:4, and a reaction was conducted for 3 hours while stirring was conducted at a temperature of 110° C. and the generated water was removed. The solvent was removed by distillation under a reduced pressure, and the obtained residue was subjected to a recrystallization treatment by using a mixed solvent including chloroform and isopropyl alcohol at a mass ratio of 1:5. The precipitated crystal was dried at 120° C. under a reduced pressure to give the object product Compound No. 6 at a yield of 9.1%. The results of analyses for the obtained compound were as shown below.
<Results of Analyses>
($^1$H-NMR) Deuterated chloroform solvent
1.06 (d, 12), 1.68 (dt, 4), 1.79 (dtt, 2), 1.81 (s, 12), 4.00 (m, 4), 6.04 (s, 2), 7.03 (d, 2), 7.56 (s, 2), 7.60 (d, 2)
(TG) Amount of sample: 3.60 mg, measurement conditions: $N_2$; 200 ml/min, temperature raising; 10° C./min, weight loss initiation temperature; 322° C.

Example 3

Synthesis of Compound No. 9

2.1 parts by mol of 2,2,3-trimethyl-1-propyl-5-methoxy-3H-indolium iodide and 1 part by mol of squaric acid were added to a mixed solvent including toluene and butanol at a mass ratio of 1:4, and a reaction was conducted for 3 hours while stirring was conducted at a temperature of 110° C. and the generated water was removed. The solvent was distilled off under a reduced pressure, and the obtained residue was subjected to a silica gel column chromatography treatment using a mixed solvent including ethyl acetate and methanol at a mass ratio of 10:1. The component having an Rf value of 0.5 was isolated, the solvent was distilled off, and the obtained solid was dried at 120° C. under a reduced pressure to give the objective product Compound No. 9 at a yield of 33.3%. The results of analyses for the obtained compound were as shown below.
<Results of Analyses>
($^1$H-NMR) Deuterated chloroform solvent
1.28 (t, 6), 2.04 (tq, 4), 2.24 (s, 12), 3.78 (s, 6), 4.12 (t, 4), 6.79 (s, 2), 6.81 (d, 2), 6.83 (s, 2), 7.42 (d, 2)
(TG) Amount of sample: 3.29 mg, measurement conditions: $N_2$; 200 ml/min, temperature raising; 10° C./min, weight loss initiation temperature; 294° C.

Evaluation Example 1

Evaluation of Optical Property and Heat Resistance of Color Tone Correcting Agent Physical properties as a color tone correcting agent were evaluated for Compounds Nos. 3, 6 and 9 of the present invention obtained in the above-mentioned Examples 1 to 3 and resembling compounds: the following Comparative compounds 1 to 3.

In the evaluation, the maximum absorption (λmax) by the spectroscopic absorption spectrum of a chloroform solution, the light absorption coefficient (ε) and half width at λmax, and a decomposition peak temperature (measurement conditions: $N_2$; 200 ml/min, temperature raising; 10° C./min) in a DTA measurement, were measured. The results are shown in Table 1.

TABLE 1

| Color tone correcting agent | λ max (nm) | ε | Half width (nm) | Decomposition temperature (° C.) |
|---|---|---|---|---|
| Compound No. 3 | 670 | 348000 | 28 | 319 |
| Compound No. 6 | 637 | 277000 | 23 | 326 |
| Compound No. 9 | 655 | 261000 | 28 | 293 |
| Comparative Compound No. 1 | 642 | 282000 | 26 | 287 |
| Comparative Compound No. 2 | 672 | 246000 | 50 | 290 |
| Comparative Compound No. 3 | 645 | 219000 | 46 | 260 |

[Chemical Formula 16]
Comparative compound 1

TABLE 1-continued

| Color tone correcting agent | λ max (nm) | ε | Half width (nm) | Decomposition temperature (° C.) |
|---|---|---|---|---|

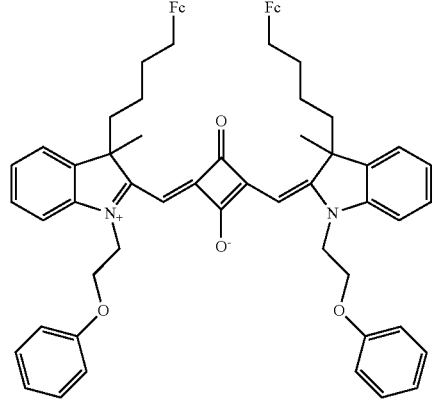

Comparative compound 2

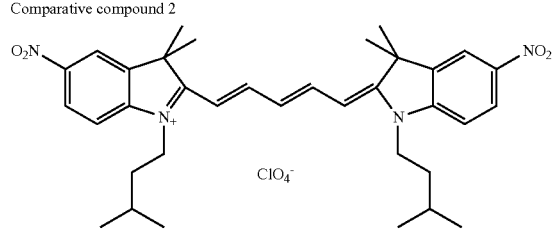

Comparative compound 3

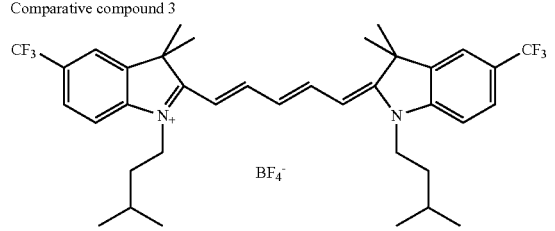

wherein, Fc is a ferrocenyl group.

It could be confirmed from the above-mentioned evaluation results that all of Compounds Nos. 3, 6 and 9 had a high decomposition temperature and were excellent in heat resistance as compared to the resembling compounds: Comparative compounds 1 to 3. Furthermore, it could also be confirmed that Compounds Nos. 3, 6 and 9 had half widths that were smaller than those of Comparative compounds 2 and 3 and similar to that of Comparative compound 1. Namely, Compounds Nos. 3, 6 and 9 of the present invention are more excellent than Compounds Nos. 1 to 3 in heat resistance, and are similar to Comparative compound 1 and more excellent than Comparative compounds 2 and 3 in steepness of light absorption.

Example 4

Production of Optical Filters Nos. 1 to 3

Pressure-sensitive adhesive solutions (coating liquids 1 to 3) were prepared by the compositions described in the following Table 2. Each of the pressure-sensitive adhesive solution was applied to a polyethylene telephthalate film having a thickness of 100 μM by using a slit coater having a thickness of 200 μm, dried at 100° C. for 10 minutes, and a glass having a thickness of 1 mm was attached to the coated surface to produce Optical filters Nos. 1 to 3 including the color tone correcting agent in the pressure-sensitive adhesive layer.

TABLE 2

| <Compositions> | |
|---|---|
| (Coating liquid 1) | |
| Solution of 0.5% by mass of Compound No. 3 in ethyl methyl ketone | 0.2 part by mass |
| Acrylic-based pressure-sensitive adhesive (DB Bond 5541: manufactured by Diabond Industry Co., Ltd.) | 5 part by mass |
| Methyl ethyl ketone | 0.99 part by mass |
| (Coating liquid 2) | |
| Solution of 0.5% by mass of Compound No. 6 in ethyl methyl ketone | 0.2 part by mass |
| Acrylic-based pressure-sensitive adhesive (DB Bond 5541: manufactured by Diabond Industry Co., Ltd.) | 5 part by mass |
| Methyl ethyl ketone | 0.99 part by mass |
| (Coating liquid 3) | |
| Solution of 0.5% by mass of Compound A in ethyl methyl ketone | 0.2 part by mass |
| Acrylic-based pressure-sensitive adhesive (DB Bond 5541: manufactured by Diabond Industry Co., Ltd.) | 5 part by mass |
| Methyl ethyl ketone | 0.99 part by mass |

[Chemical Formula 17]
Compound A

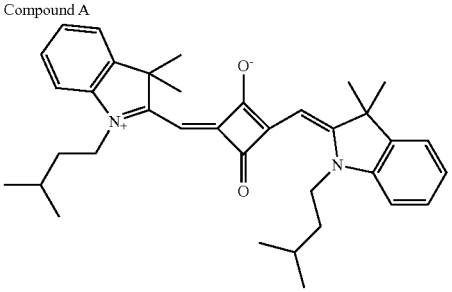

Comparative Example 1

Production of Comparative Optical Filters 1 to 3

Pressure-sensitive adhesive solutions (Comparative coating liquids 1 to 3) were prepared by the compositions described in the following Table 3. Each of the pressure-sensitive adhesive solution was applied to a polyethylene telephthalate film having a thickness of 100 μm by using a slit coater having a thickness of 200 μm, dried at 100° C. for 10 minutes, and a glass having a thickness of 1 mm was attached to the coated surface to produce Comparative optical filters Nos. 1 to 3 including the color tone correcting agent in the pressure-sensitive adhesive layer.

TABLE 3

| <Compositions> | |
|---|---|
| (Comparative coating liquid 1) | |
| Solution of 0.25% by mass of Comparative compound No. 1 in ethyl methyl ketone | 0.4 part by mass |
| Acrylic-based pressure-sensitive adhesive (DB Bond 5541: manufactured by Diabond Industry Co., Ltd.) | 5 part by mass |
| Methyl ethyl ketone | 0.99 part by mass |
| (Comparative coating liquid 2) | |
| Solution of 0.25% by mass of Comparative compound No. 2 in ethyl methyl ketone | 0.4 part by mass |

TABLE 3-continued

| <Compositions> | |
|---|---|
| Acrylic-based pressure-sensitive adhesive (DB Bond 5541: manufactured by Diabond Industry Co., Ltd.) | 5 part by mass |
| Methyl ethyl ketone | 0.99 part by mass |
| (Comparative coating liquid 3) | |
| Solution of 0.5% by mass of Comparative compound No. 3 in ethyl methyl ketone | 0.2 part by mass |
| Acrylic-based pressure-sensitive adhesive (DB Bond 5541: manufactured by Diabond Industry Co., Ltd.) | 5 part by mass |
| Methyl ethyl ketone | 0.99 part by mass |

Evaluation Example 2

Evaluation of Heat Resistance of Optical Filter

For the optical filters obtained in the above-mentioned Example 4 and Comparative Example 1, the absorption spectrum immediately after the formation of the optical filter was measured by an ultraviolet-visible-near infrared spectrophotometer V-570 manufactured by JASCO Corporation, and λmax and a half width were measured. Furthermore, the transmittance at λmax after conducting a heat resistance test under the following conditions (transmittance after heat resistance test) and the transmittance before the heat resistance test were measured, and the ratio thereof "(100−transmittance after heat resistance test/100−transmittance before heat resistance test)×100(%)" was calculated and used as the heat resistance (%) of the optical filter. The results are shown in Table 4.

(Heat Resistance Test)

The optical filter was heated at 80° C. in a thermostatic bath for 50 hours.

TABLE 4

| Optical filter | Compound | λ max (nm) | Half width (nm) | Thermal resistance (%) |
|---|---|---|---|---|
| Optical filter No. 1 | Compound No. 3 | 670 | 44 | 86.2 |
| Optical filter No. 2 | Compound No. 6 | 637 | 44 | 87.3 |
| Optical filter No. 3 | Compound No. A | 638 | 40 | 84.0 |
| Comparative optical filter No. 1 | Comparative compound 1 | 644 | 40 | 77.7 |
| Comparative optical filter No. 2 | Comparative compound 2 | 671 | 90 | 7.5 |
| Comparative optical filter No. 3 | Comparative compound 3 | 643 | 73 | 40.4 |

It could be confirmed from the above-mentioned Table 4 that Optical filters Nos. 1 to 3, the optical filters of the present invention, are more excellent than Comparative optical filters 1 to 3 in heat resistance. Furthermore, it could also be confirmed that the half widths were similar to or slightly broader than that of Comparative optical filter 1 and smaller than those of Comparative optical filters 2 and 3.

Evaluation Example 3

Evaluation of Light Resistance of Optical Filter

A light resistance test under the following conditions was conducted for Optical filters Nos. 1 to 3 obtained in the above-mentioned Example 4, and the light absorbance at λmax after conducting a light resistance test under the following conditions (transmittance after light resistance test) and the transmittance before the light resistance test were measured, and the ratio thereof "(100−transmittance after light resistance test/100−transmittance before light resistance test)×100(%)" was calculated and used as the light resistance (%) of the optical filter. The results are shown in Table 5.

(Light Resistance Test)

The optical filter was irradiated with light of 55,000 lx from a xenon light source for 50 hours.

TABLE 5

| Optical filter | Compound | Light resistance (%) |
|---|---|---|
| Optical filter No. 1 | Compound No. 3 | 67.8 |
| Optical filter No. 2 | Compound No. 6 | 64.9 |
| Optical filter No. 3 | Compound No. A | 39.9 |

It could be confirmed from the above-mentioned Table 5 that, when the compounds according to the present invention are compared, the optical filters using Compound No. 3 and Compound No. 6 as a color tone correcting agent have better light resistance than the optical filter using Compound A as a color tone correcting agent.

The invention claimed is:

1. An optical filter, comprising a color tone correcting squarylium compound having general formula (2):

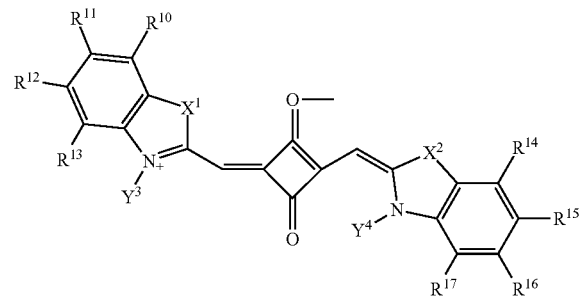

(2)

wherein at least one of $R^{10}$, $R^{11}$, $R^{12}$, and $R^{13}$ is a nitro group, an alkyl group having 1 to 4 carbon atom(s), a halogen-substituted alkyl group having 1 to 4 carbon atom(s), an alkoxy group having 1 to 4 carbon atom(s) or a halogen-substituted alkoxy group having 1 to 4 carbon atom(s), and other is/are each a hydrogen atom, at least one of $R^{14}$, $R^{15}$, $R^{16}$, and $R^{17}$ is a nitro group, an alkyl group having 1 to 4 carbon atom(s), a halogen-substituted alkyl group having 1 to 4 carbon atom(s), an alkoxy group having 1 to 4 carbon atom(s) or a halogen-substituted alkoxy group having 1 to 4 carbon atom(s), and other is/are each a hydrogen atom, $X^1$ and $X^2$ each represents —$CR^{53}R^{54}$—, wherein $R^{53}$ and $R^{54}$ each represents an alkyl group having 1 to 20 carbon atom(s) optionally substituted by a hydroxyl group, a halogen atom, a cyano group or a nitro group, and $Y^3$ and $Y^4$ each represents a hydrogen atom, an alkyl group having 1 to 20 carbon atom(s) optionally substituted by a hydroxyl group, a halogen atom, a cyano group or a nitro group, an aryl group having 6 to 30 carbon atoms optionally substituted by a hydroxyl group, a halogen atom, a cyano group or a nitro group, or an arylalkyl group having 7 to 30 carbon atoms optionally substituted by a hydroxyl group, a halogen atom, a cyano group or a nitro group, wherein the methylene group(s) in the alkyl groups and arylalkyl groups in the $Y^3$ and $Y^4$ may be interrupted by —O—, —S—, —CO—, —COO—, —OCO—, —SO$_2$—, —NH—, —CONH—, —NHCO—, —N=CH— or —CH=CH—.

2. The optical filter according to claim 1, wherein the squarylium compound has general formula (3):

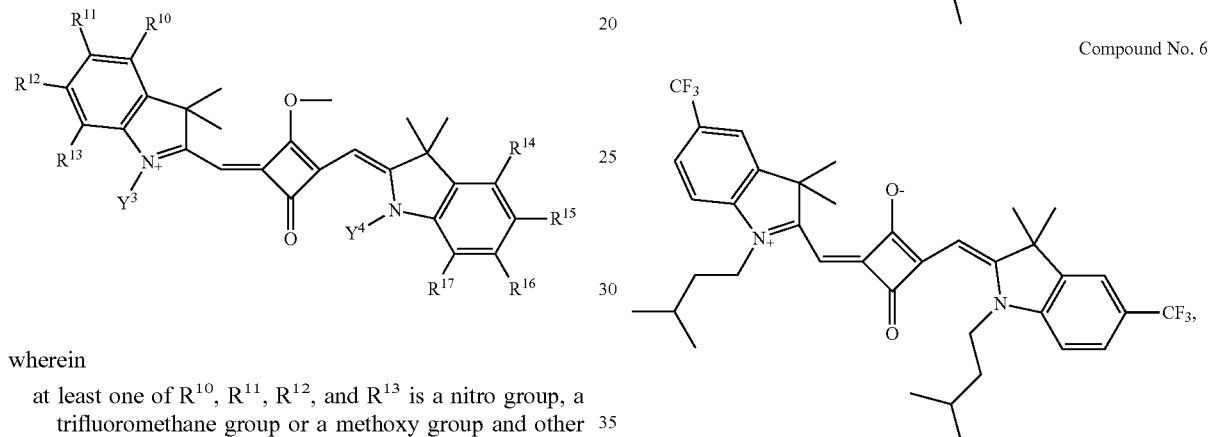

(3)

wherein
at least one of $R^{10}$, $R^{11}$, $R^{12}$, and $R^{13}$ is a nitro group, a trifluoromethane group or a methoxy group and other is/are each a hydrogen atom, at least one of $R^{14}$, $R^{15}$, $R^{16}$, and $R^{17}$ is a nitro group or a trifluoromethane group and other is/are each a hydrogen atom, and $Y^3$ and $Y^4$ have the same meanings as those defined for the general formula (2).

3. The optical filter according to claim 1, wherein the squarylium compound has general formula (4):

(4)

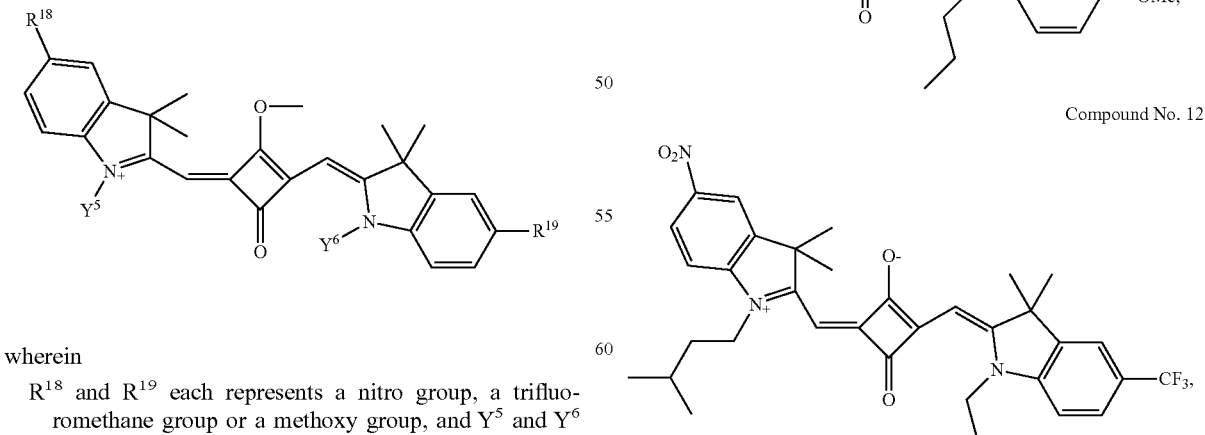

wherein
$R^{18}$ and $R^{19}$ each represents a nitro group, a trifluoromethane group or a methoxy group, and $Y^5$ and $Y^6$ each represents an alkyl group having 1 to 18 carbon atom(s), an ether group having 3 to 18 carbon atoms, an aryl group having 6 to 18 carbon atoms or an arylalkyl group having 7 to 18 carbon atoms.

4. A squarylium compound selected from the group consisting of:

Compound No. 3

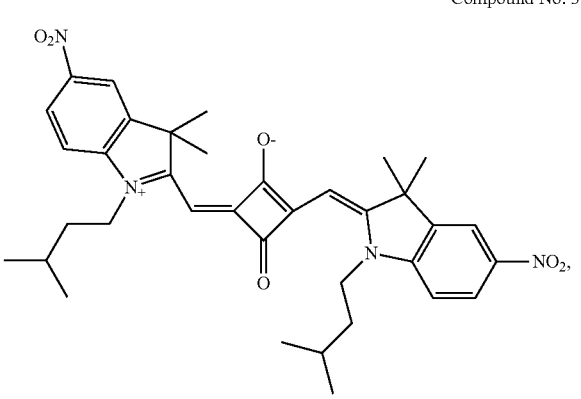

Compound No. 6

Compound No. 9

Compound No. 12

Compound No. 15
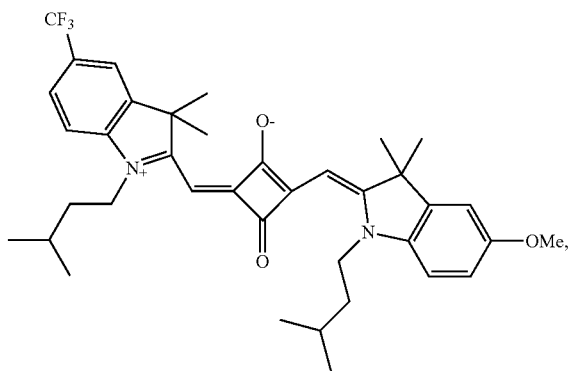
Compound No. 18
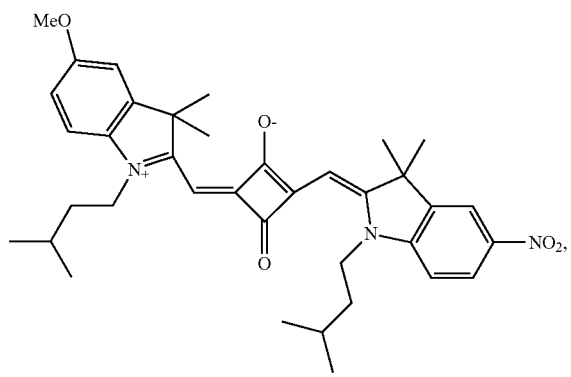
Compound No. 22
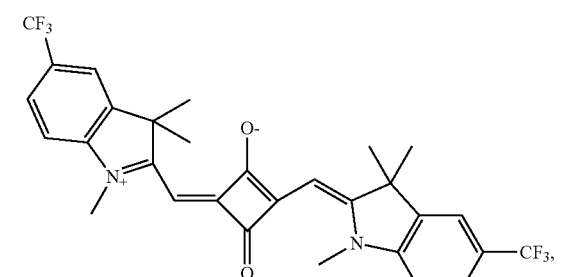
Compound No. 23
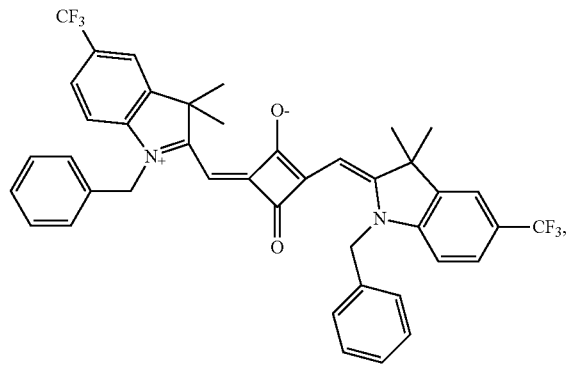
Compound No. 24
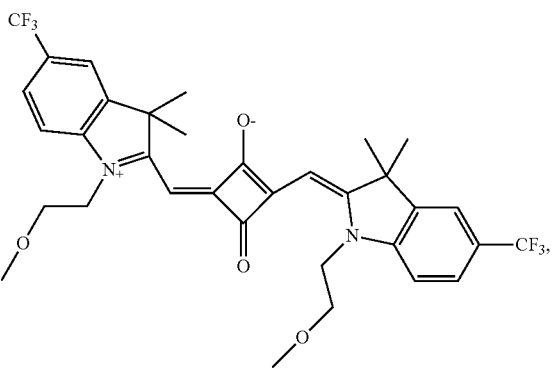
Compound No. 25
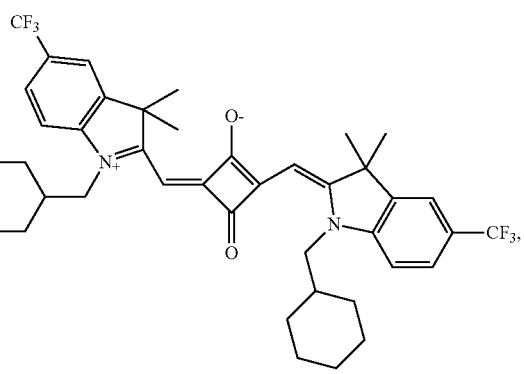
Compound No. 26
Compound No. 33
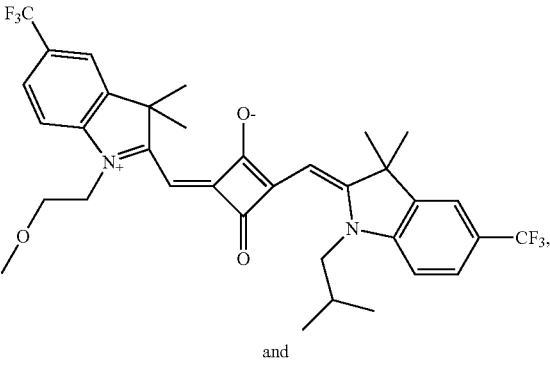
and Compound No. 35

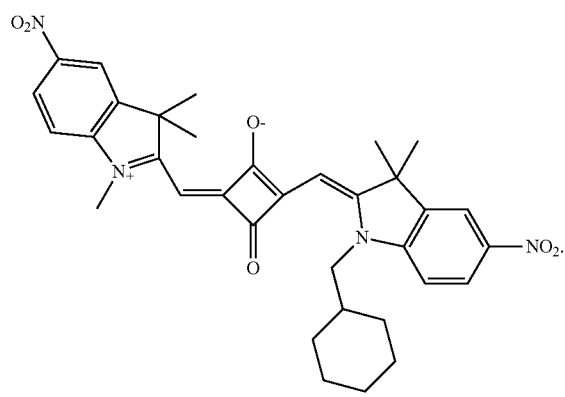

Compound No. 3

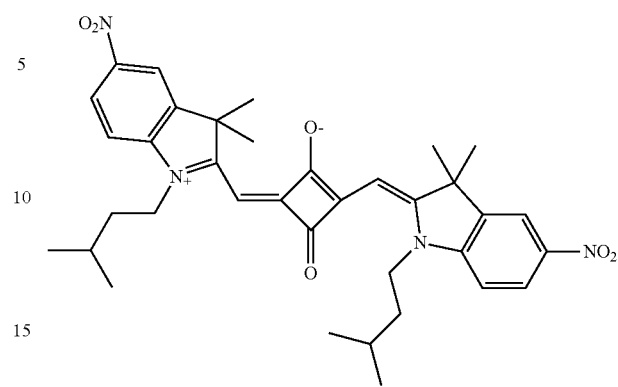

5. The optical filter according to claim 1, configured in an image display apparatus or an illumination apparatus.
6. The optical filter according to claim 2, configured in an image display apparatus or an illumination apparatus.
7. The optical filter according to claim 3, configured in an image display apparatus or an illumination apparatus.
8. The optical filter according to claim 1, wherein the squarylium compound is selected from the group consisting of:

Compound No. 1

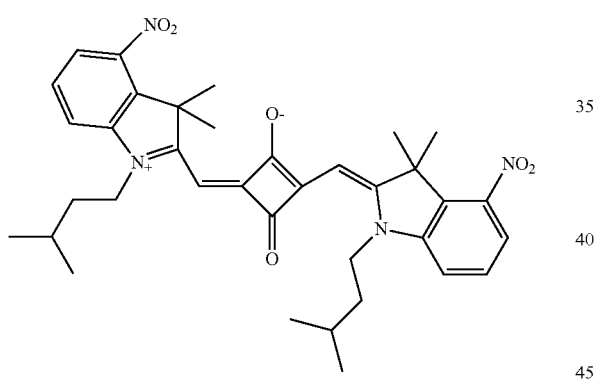

Compound No. 4

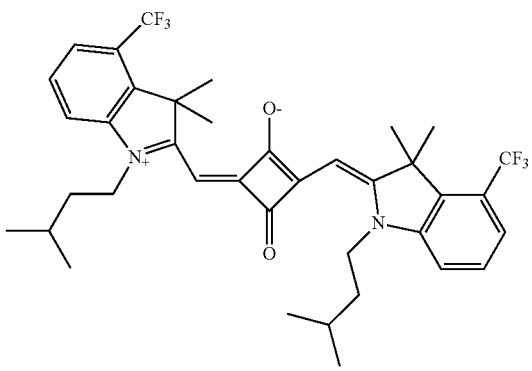

Compound No. 2

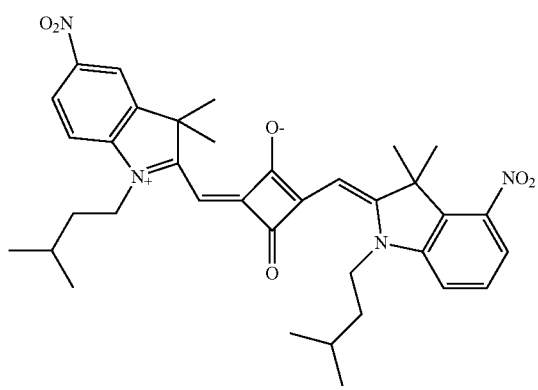

Compound No. 5

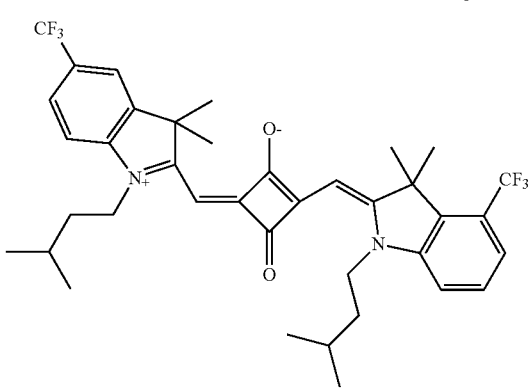

Compound No. 6
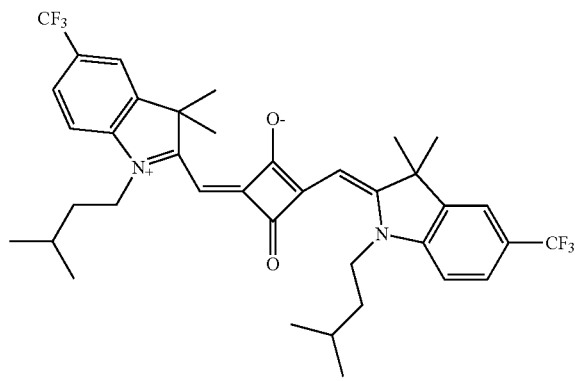
Compound No. 7
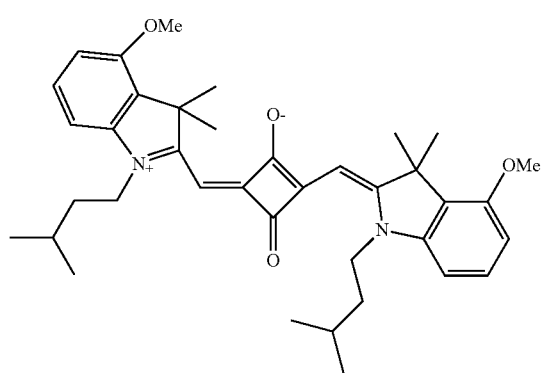
Compound No. 8
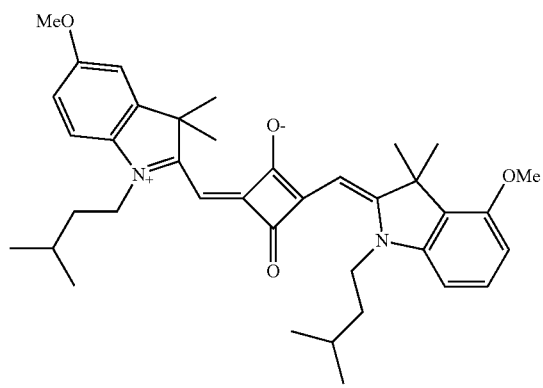
Compound No. 9
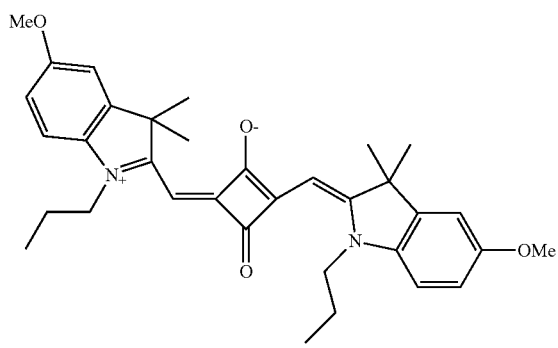
Compound No. 10
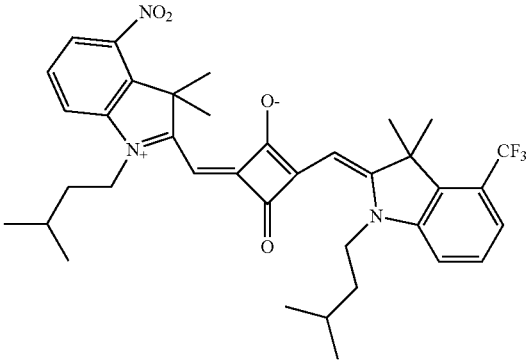
Compound No. 11
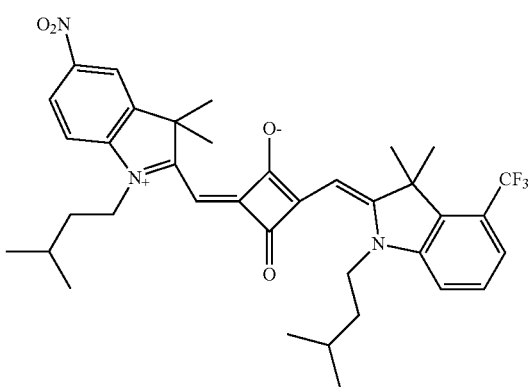
Compound No. 12
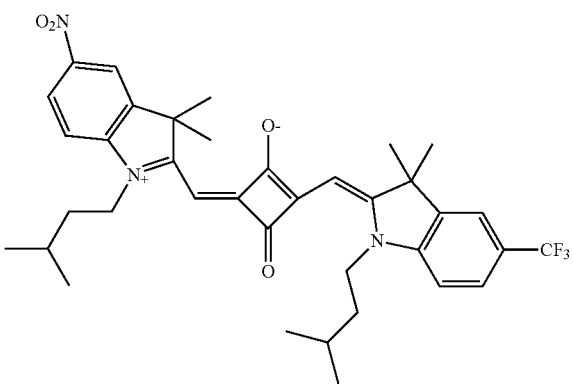
Compound No. 13
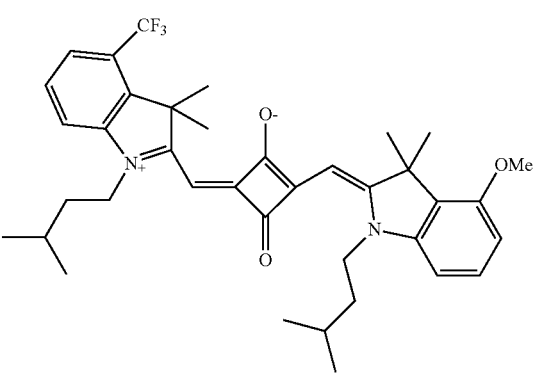

Compound No. 14
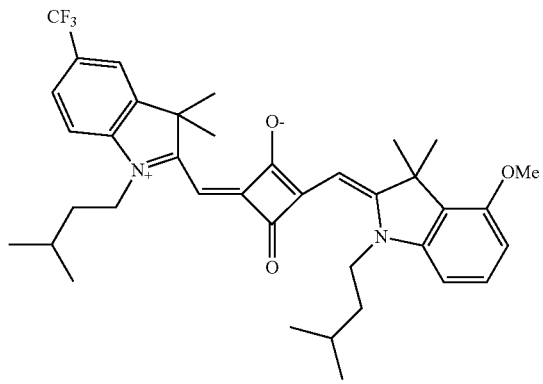
Compound No. 15
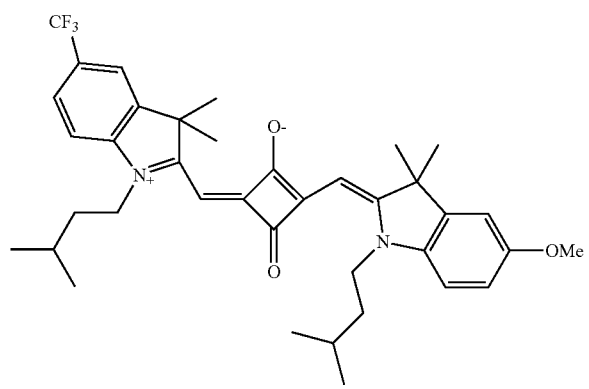
Compound No. 16
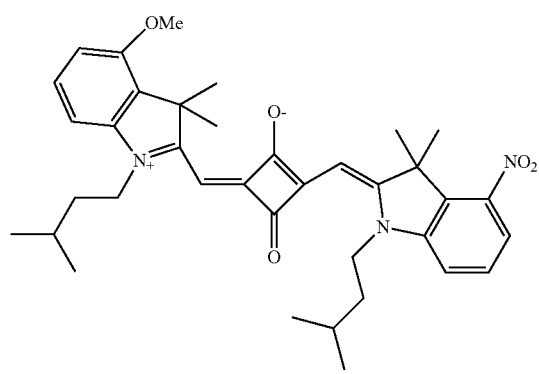
Compound No. 17
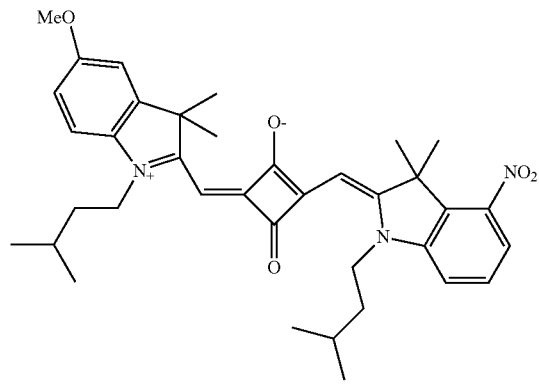
Compound No. 18
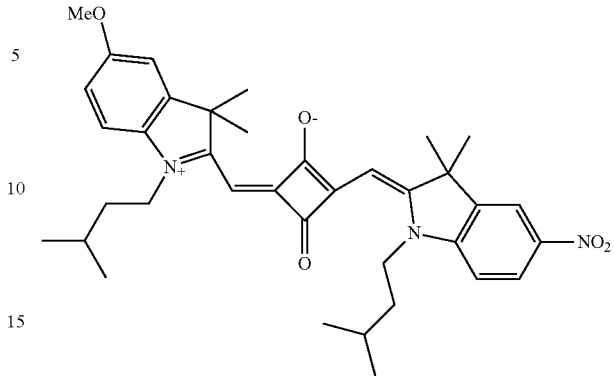
Compound No. 19
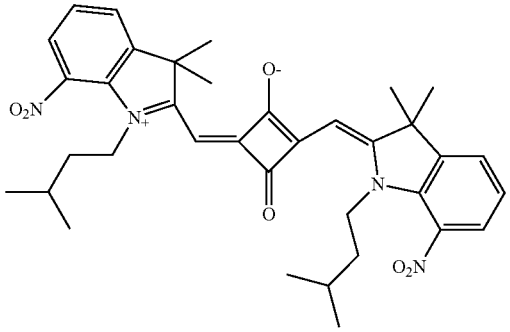
Compound No. 20
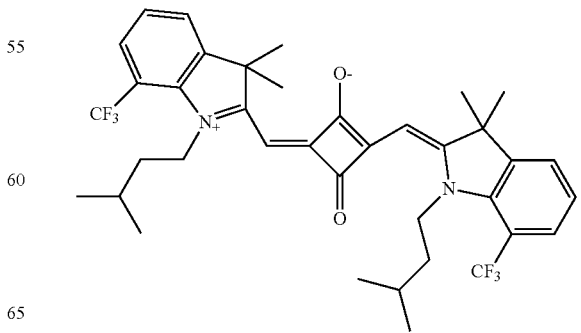

Compound No. 21
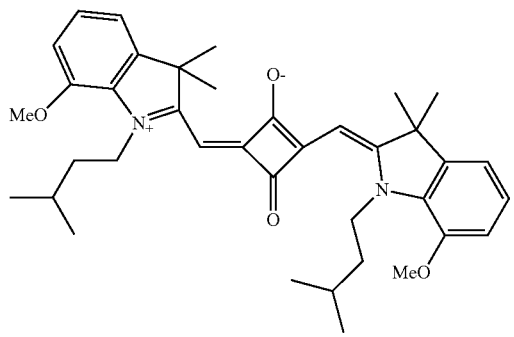
Compound No. 25
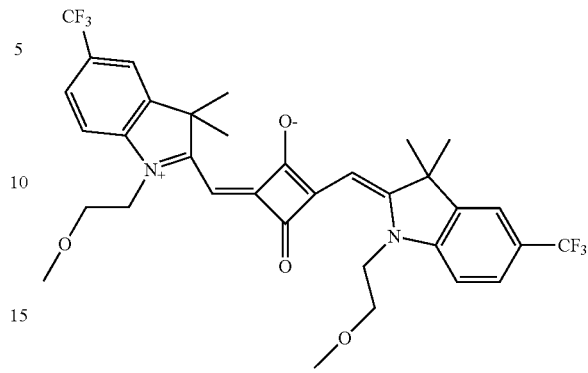
Compound No. 22
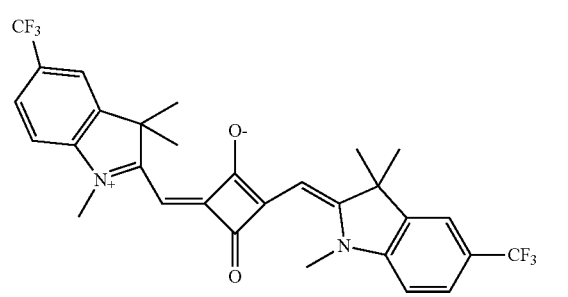
Compound No. 26
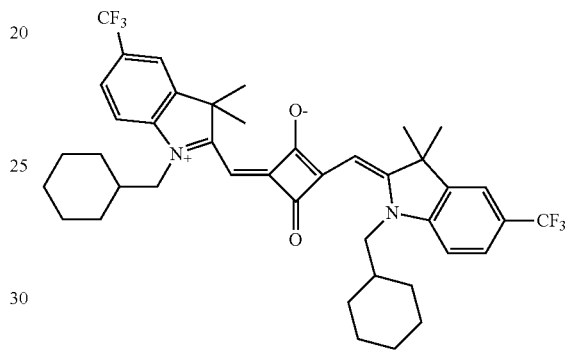
Compound No. 23
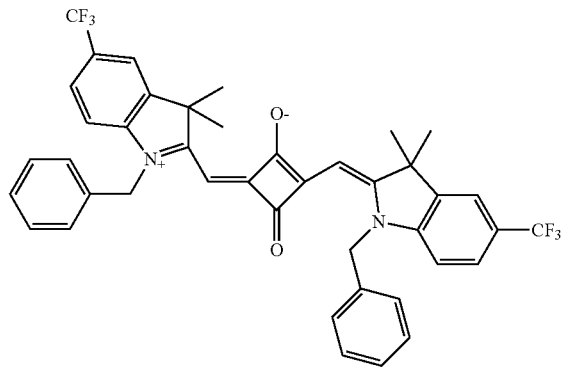
Compound No. 27
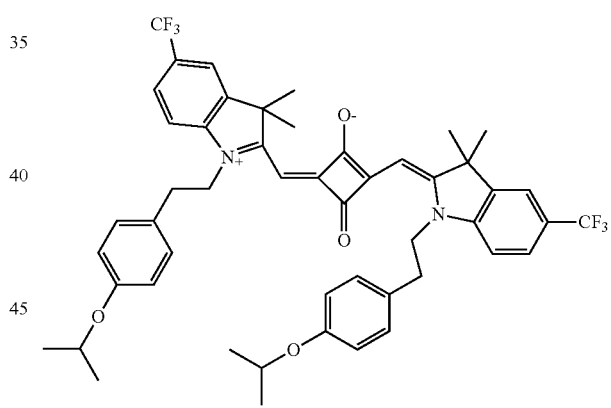
Compound No. 24
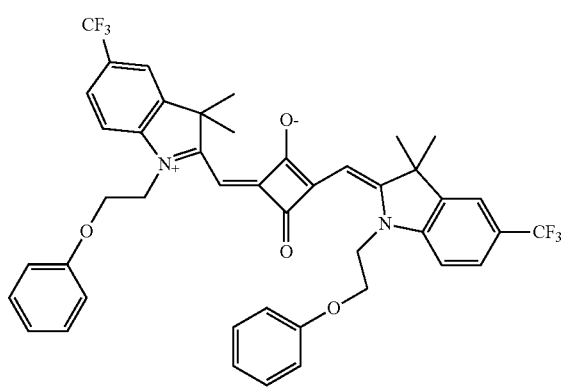
Compound No. 28
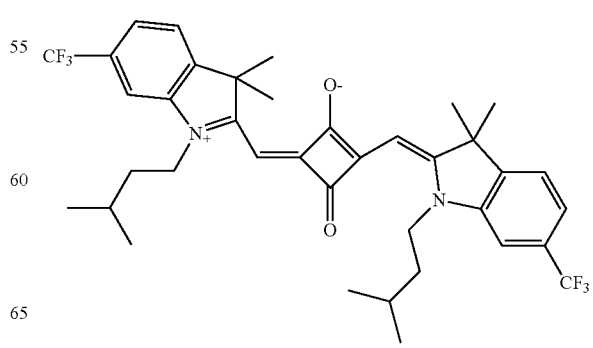

Compound No. 29
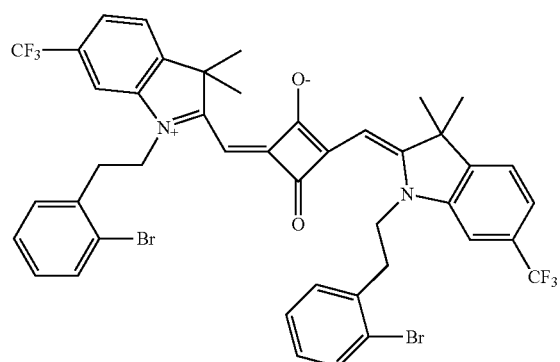
Compound No. 30
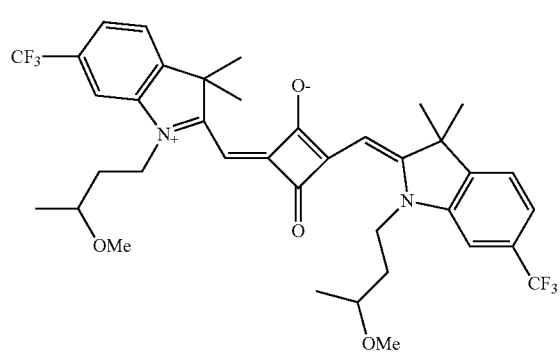
Compound No. 31
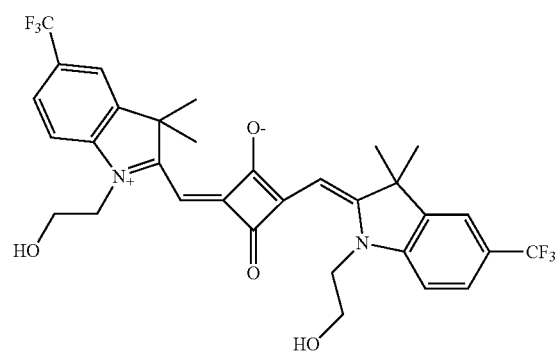
Compound No. 32
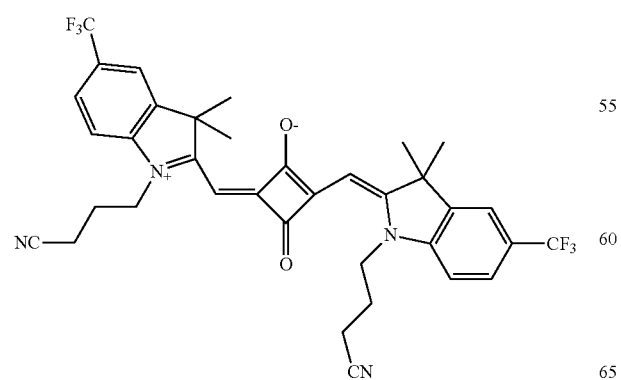
Compound No. 33
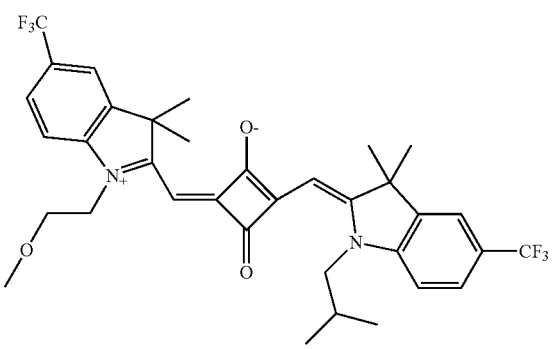
Compound No. 34
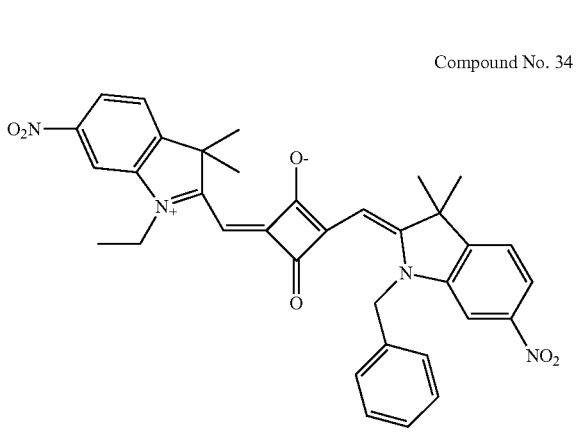
Compound No. 35
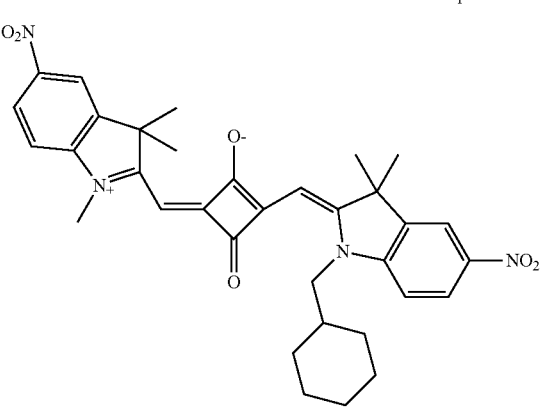
Compound No. 36
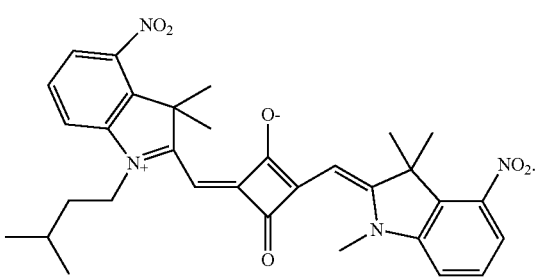

9. The optical filter according to claim 1, wherein the squarylium compound is selected from the group consisting of:
Compound No. 3
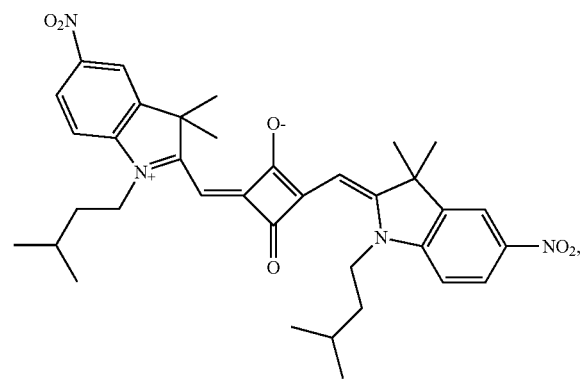
Compound No. 6
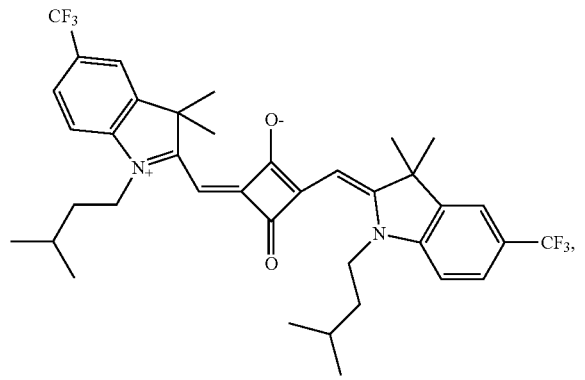
Compound No. 9
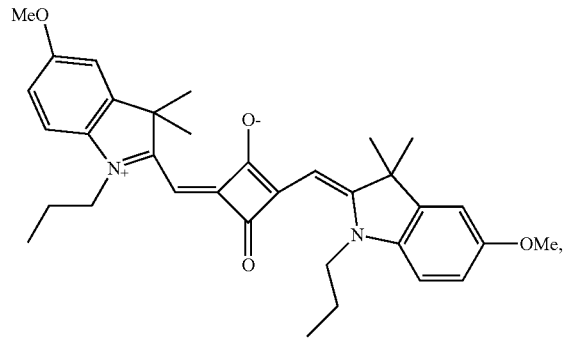
Compound No. 12
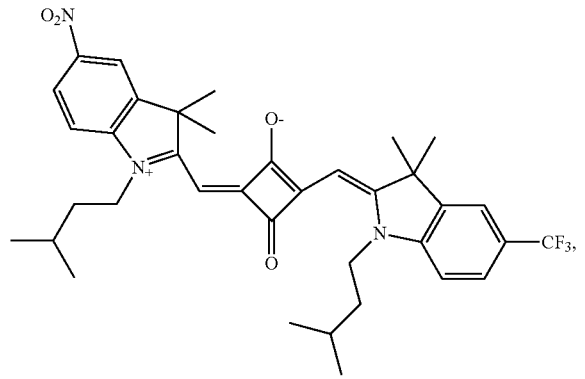
-continued
Compound No. 15
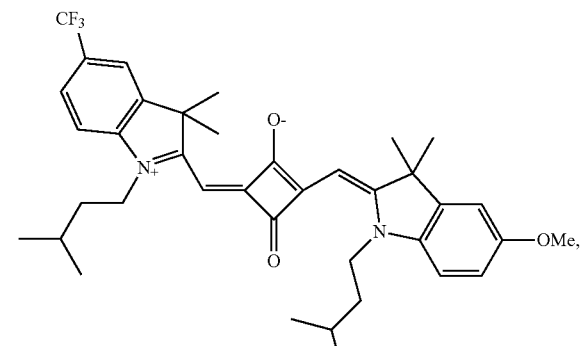
Compound No. 18
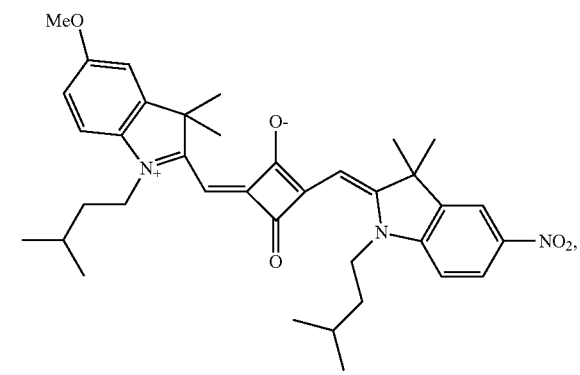
Compound No. 22
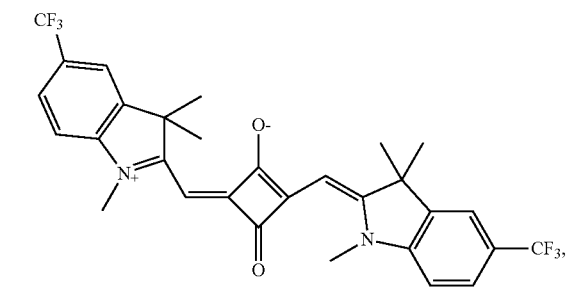
Compound No. 23
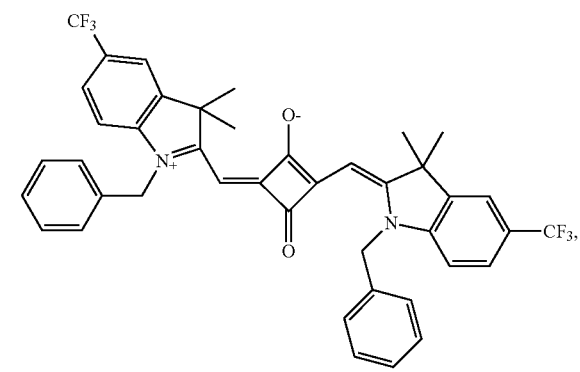

-continued
Compound No. 24
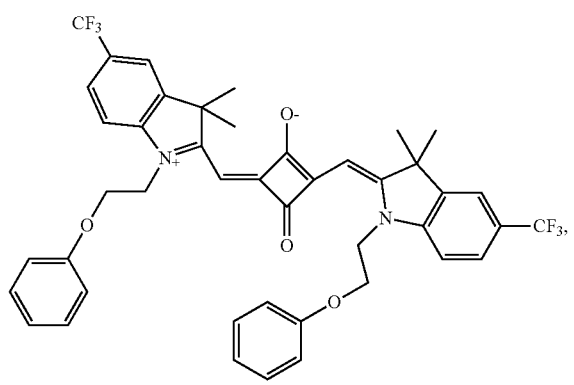
Compound No. 25
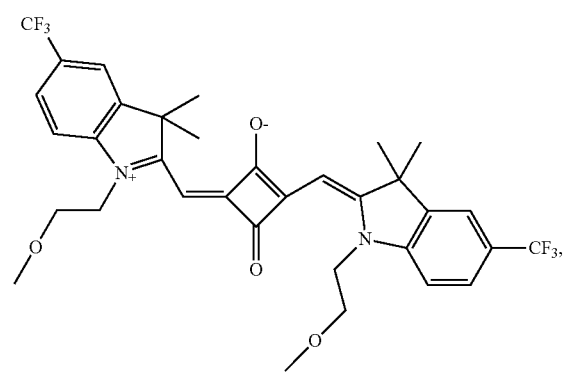
Compound No. 26
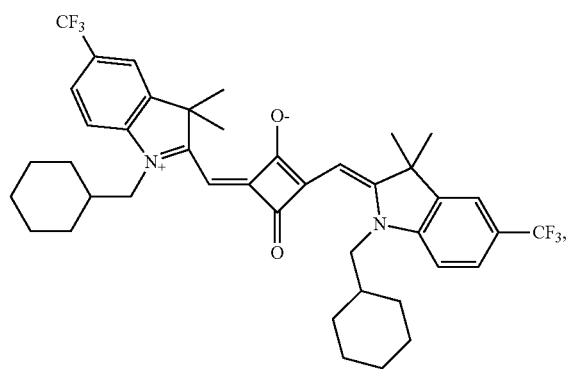
-continued
Compound No. 33
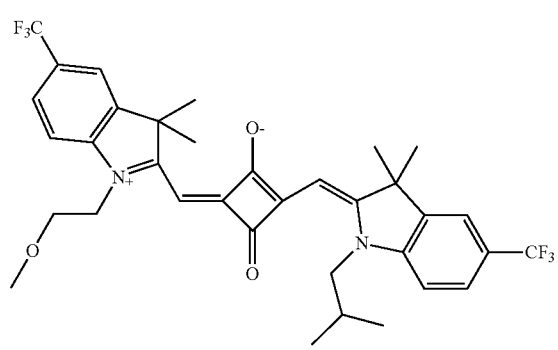
and
Compound No. 35
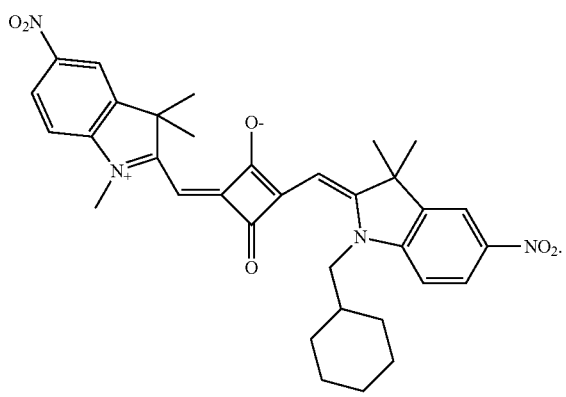
* * * * *